US010803382B2

(12) United States Patent
Tayebi et al.

(10) Patent No.: US 10,803,382 B2
(45) Date of Patent: Oct. 13, 2020

(54) GAS IDENTIFICATION APPARATUS AND MACHINE LEARNING METHOD

(71) Applicant: Intel Corporation, Santa Clara, CA (US)

(72) Inventors: Noureddine Tayebi, Santa Clara, CA (US); Varvara Kollia, Mountain View, CA (US); Pradyumna S. Singh, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 495 days.

(21) Appl. No.: 15/625,997

(22) Filed: Jun. 16, 2017

(65) Prior Publication Data

US 2018/0365559 A1    Dec. 20, 2018

(51) Int. Cl.
    *G06N 3/08*     (2006.01)
    *G01N 33/00*    (2006.01)
    (Continued)

(52) U.S. Cl.
    CPC .............. *G06N 3/08* (2013.01); *G01N 27/14* (2013.01); *G01N 33/0047* (2013.01);
    (Continued)

(58) Field of Classification Search
    None
    See application file for complete search history.

(56) References Cited

U.S. PATENT DOCUMENTS 4,457,161 A    7/1984  Iwanaga et al.
4,638,443 A    1/1987  Kaneyasu et al.
(Continued)

FOREIGN PATENT DOCUMENTS

CN    1947007 A    4/2007
EP    2778667 A1   9/2014
(Continued)

OTHER PUBLICATIONS

Xiajing Shi, Lingyan Wang, Nancy Kariuki, Jin Luo, Chuan-Jian Zhong, Susan Lu; "A multi-module artificial neural network approach to pattern recognition with optimized nanostructured sensor array" Sensors and Actuators B 117; pp. 65-73 (Year: 2006).*
(Continued)

*Primary Examiner* — Gregory J Toatley, Jr.
*Assistant Examiner* — Terence E Stifter, Jr.
(74) *Attorney, Agent, or Firm* — Schwabe, Williamson & Wyatt, P.C.

(57) ABSTRACT

Embodiments herein relate to gas identification with a gas identification apparatus having a plurality of metal oxide semiconductor (MOS) sensors. In various embodiments, a gas identification apparatus may include a set of heterogeneous MOS sensors to provide different response patterns for the presence of different gases and an identification engine coupled with the sensors, and having a plurality of regression models and one or more artificial neural networks, to analyze a response pattern to identify presence of a gas, based at least in part on a plurality of property measurements of the MOS sensors when exhibiting the response pattern, and using one or more of the plurality of regression models and the one or more artificial neural networks. Other embodiments may be described and/or claimed.

16 Claims, 11 Drawing Sheets

(51) Int. Cl.
  G01N 27/14    (2006.01)
  G06F 17/18    (2006.01)
  H04L 29/08    (2006.01)
  G06N 20/00    (2019.01)
  G06N 3/04     (2006.01)
  G06N 20/10    (2019.01)
(52) U.S. Cl.
  CPC .......... G06F 17/18 (2013.01); G06N 3/0454 (2013.01); G06N 20/00 (2019.01); H04L 67/10 (2013.01); H04L 67/12 (2013.01); *G06N 20/10* (2019.01)

(56) References Cited

U.S. PATENT DOCUMENTS

| | | | |
|---|---|---|---|
| 4,703,646 | A | 11/1987 | Muller et al. |
| 4,847,783 | A | 7/1989 | Grace et al. |
| 5,019,885 | A | 5/1991 | Yagawara et al. |
| 6,085,576 | A | 7/2000 | Sunshine et al. |
| 9,823,211 | B1 * | 11/2017 | Allen ............... G01N 33/0031 |
| 2005/0045477 | A1 | 3/2005 | Wei et al. |
| 2005/0097941 | A1 | 5/2005 | Sandvik et al. |
| 2007/0202012 | A1 * | 8/2007 | Steichen ........... G01N 33/0031 422/98 |
| 2008/0302672 | A1 | 12/2008 | Sandvik et al. |
| 2014/0197851 | A1 | 7/2014 | Astley et al. |
| 2014/0260546 | A1 | 9/2014 | Chen et al. |
| 2015/0323510 | A1 * | 11/2015 | Huynh ............... H01L 23/3157 73/23.34 |
| 2016/0187279 | A1 * | 6/2016 | Tayebi ............... G01N 27/16 73/23.21 |

FOREIGN PATENT DOCUMENTS

| | | |
|---|---|---|
| TW | 285801 B | 9/1996 |
| TW | 587165 B | 5/2004 |
| WO | 2005073715 A1 | 8/2005 |
| WO | 2012084343 A1 | 6/2012 |
| WO | 2016/105921 A1 | 6/2016 |

OTHER PUBLICATIONS

Health Organization Global Health Observatory (GHO) Data (2017). Retrieved on Jul. 7, 2017 from URL <<http://www.who.int/gho/phe/en/>>.
R. Kessler. Prevention: Air of danger. Nature (2014), 509, S62-S63.
H. Chen et al. Long-term exposure to traffic-related air pollution and cardiovascular mortality. Epidemiolog (Cambridge, Mass.) (2013), 24, 35-43.
R. D. Brook et al., Air pollution and cardiovascular disease: a statement for healthcare professionals from the Expert Panel on Population and Prevention Science of the American Heart Association. Circulation (2004), 109, 2655-2671.
K.K. Shukla, R.R. Das, R. Dwivedi, Adaptive resonance neural classifier for identification of gases/odours using an integrated sensor array, Sensors and Actuators B 50 (1998) 194-203.
E. Kim, S. Lee , J. H. Kim , C. Kim , Y. T. Byun, H. S. Kim and T. Lee 1, Pattern Recognition for Selective Odor Detection with Gas Sensor Arrays, Sensors 2012, 12, 16262-16273; doi:10.3390/s121216262.
W. Khalaf, C. Pace, M. Gaudioso, Gas Detection via Machine Learning, World Academy of Science, Engineering and Technology International Journal of Computer, Electrical, Automation, Control and Information Engineering 2, 1, 2008.
R. Gutierrez-Osuna. Pattern analysis for machine olfaction: a review. IEEE Sensors Journal (2002), 2, 189-202.
R. Kabacoff (2017). Multiple Linear Regression. Retrieved on Jul. 7, 2017 from URL <<http://www.statmethods.net/stats/regression.html.>>.
Stanford. CS229 Machine Learning Autumn 2016. Retrieved on Jul. 7, 2017 from URL <<http://cs229.stanford.edu/>>.
K. A. Ngo, P. Lauque, K. Aguir. High performance of a gas identification system using sensor array and temperature modulation. Sensors and Actuators B: Chemical (2007), 124, 209-216.
J. C. Chen, C. J. Liu, Y. H. Ju. Determination of the composition of NO2 and NO mixture by thin film sensor and back-propagation network. Sensors and Actuators B: Chemical (2000), 62, 143-147. retrieved from URL <http://wwwsciencedirect.com/science/article/pii/S0925400599003780.>>.
The R Project for Statistical Computing. Retrieved on Jul. 7, 2017 from URL <<https://www.R-project.org/.>>.
N. Barsan, D. Koziej, U. Weimar. "Metal oxide-based gas sensor research: How to?" Sensors and Actuators B 121 , (2007)18-35.
C. Wang, et al., Metal Oxide Gas Sensors: Sensitivity and Influencing Factors; Sensors; Mar. 15, 2010; pp. 2088-2106; vol. 10; MDPI.
International Search Report and Written Opinion, dated Mar. 14, 2016, issued in related International Application PCT/US2015/064332; filed Dec. 7, 2015, 14 pages.
Figaro Engineering Inc., Retrieved on Jul. 7, 2017 from URL <<http://www.figaro.co.jp/en/>>.
AMS AG (2017). Retrieved on Jul. 31, 2017from URL <<https://www.appliedsensor.com/>>.
Synkera Technologies Inc., Retrieved on Jul. 7, 2017 from URL <<http://www.synkerainc.com/>>.
Sensirion the Sensor Company (2017). Retrieved on Jul. 7 2017 form URL <<http://sensirion.com.>>.

* cited by examiner

GAS IDENTIFICATION APPARATUS AND MACHINE LEARNING METHOD

FIELD

Embodiments of the present disclosure generally relate to the field of gas identification and, more particularly, to gas identification techniques with metal oxide semiconductor (MOS) sensors and to the field of machine learning.

BACKGROUND

Many legacy approaches to the selective and sensitive detection of pollutant gases and volatile organic compounds (VOCs) are difficult to miniaturize. This poses a disadvantage for potential applications such as monitoring the air quality of micro-environments and/or incorporation into internet of things (IoT) nodes for the control of air pollution using dense wireless sensor networks. Additionally, some legacy approaches rely on complicated modulation techniques that require extensive pre-processing and typically require a large amount of data. This increases the power requirements for on-device analytics, which is a disadvantage for miniaturized, dense wireless sensor networks.

BRIEF DESCRIPTION OF THE DRAWINGS

Embodiments of the gas identification devices and methods of the present disclosure may overcome these limitations. The techniques will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
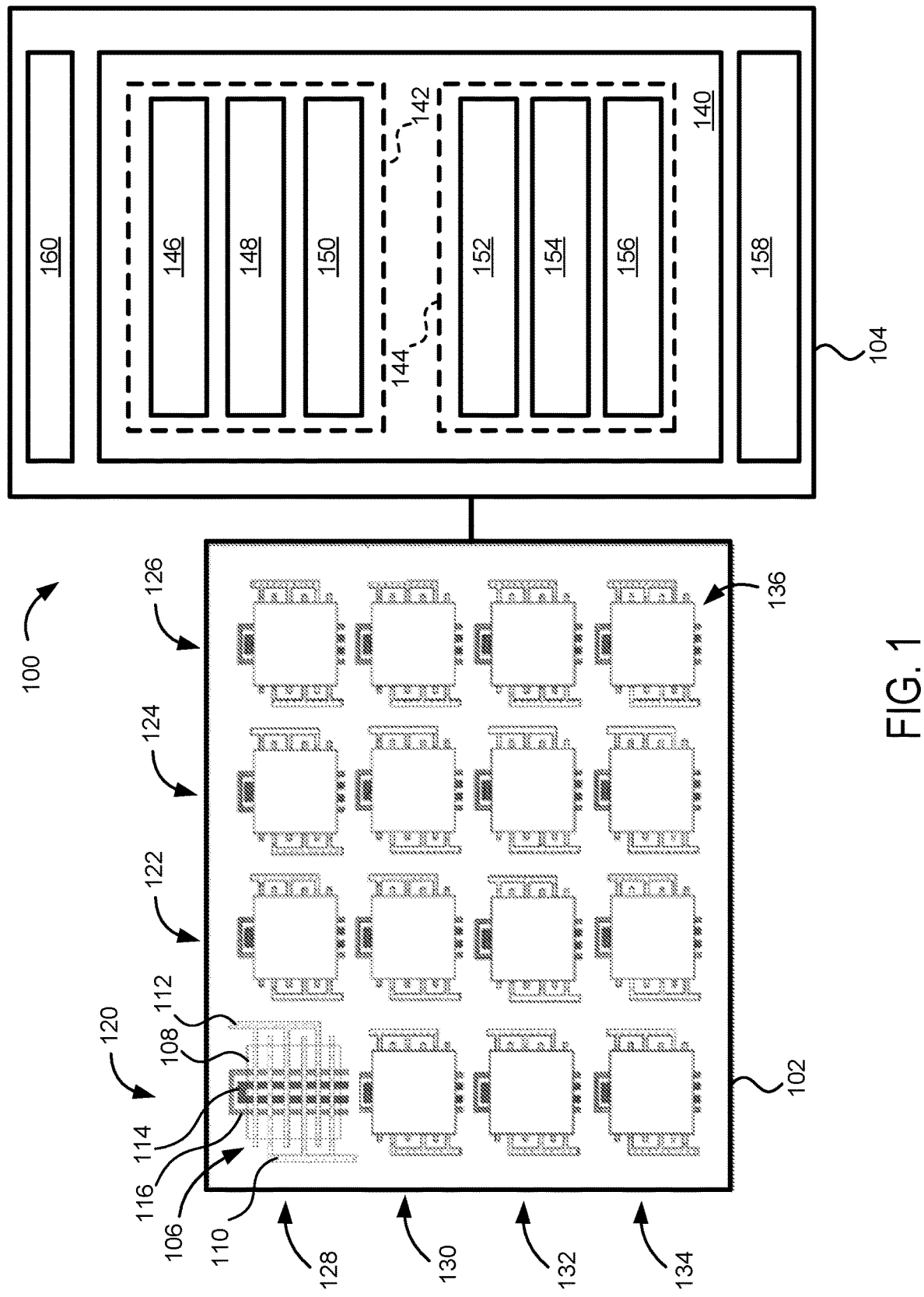
FIG. 1 is a block diagram of a gas identification apparatus with hybrid multi-staged machine learning, according to various embodiments.

Embodiments of the present disclosure describe devices, systems, and techniques to identify presence of a gas in a gas mixture with a gas identification apparatus. In various embodiments, a gas identification apparatus may include a set of heterogeneous metal oxide semiconductor (MOS) sensors to provide different response patterns for the presence of different gases and an identification engine coupled with the sensors, and having a plurality of regression models and one or more artificial neural networks, to analyze a response pattern to identify presence of a gas, based at least in part on a plurality of property measurements of the MOS sensors when exhibiting the response pattern, and using one or more of the plurality of regression models and the one or more artificial neural networks.

In the following description, various aspects of the illustrative implementations will be described using terms commonly employed by those skilled in the art to convey the substance of their work to others skilled in the art. However, it will be apparent to those skilled in the art that embodiments of the present disclosure may be practiced with only some of the described aspects. For purposes of explanation, specific numbers, materials, and configurations are set forth in order to provide a thorough understanding of the illustrative implementations. It will be apparent to one skilled in the art that embodiments of the present disclosure may be practiced without the specific details. In other instances, well-known features are omitted or simplified in order not to obscure the illustrative implementations.

In the following detailed description, reference is made to the accompanying drawings that form a part hereof, wherein like numerals designate like parts throughout, and in which is shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical or electrical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

As used herein, the term "module" may refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable components that provide the described functionality.

FIG. 1 is a block diagram of a gas identification apparatus 100, according to various embodiments. In some embodiments, the gas identification apparatus 100 may use hybrid multi-staged machine learning to estimate a concentration level of one or more gases in a mixture of gases (e.g., in air or in exhaust gases from a factory). Although the gas identification apparatus 100 is primarily described below with respect to the detection, identification, estimation of concentration level, classification into concentration ranges, and/or other actions in relation to one or more analytes in the form of gases, it should be understood that the gas identification apparatus 100 may be used to perform one or more of those actions in relation to one or more analytes that may not be gases (e.g., airborne inorganic molecules, airborne organic molecules, airborne particulate matter, or any other analyte for which detection is sought, including combinations thereof). In some embodiments, the gas identification apparatus may be used to detect and/or estimate concentration levels of one or more analytes designated as criteria air pollutants by the United States Environmental Protection Agency (EPA) (e.g., ozone ($O_3$), carbon monoxide (CO), sulfur dioxide ($SO_2$), particulate matter, lead (Pb), and/or nitrogen dioxide ($NO_2$)).

In some embodiments, the gas identification apparatus 100 may include a MOS sensor array 102 coupled with a gas identification engine 104. In various embodiments, the MOS sensor array 102 may include a set of MOS sensors that may include MOS active materials formed of various metal oxide materials (e.g., indium oxide ($In_2O_3$), tin oxide ($SnO_2$), tungsten oxide ($WO_3$), zinc oxide (ZnO), or any other suitable metal oxide material). Non-limiting examples of other metal oxide materials may include $V_2O_5$, $CR_{2-x}Ti_x O_{3+z}$, $TeO_2$, $TiO_2$, CuO, $CeO_2$, $Al_2O_3$, $V_2O_3$, $Fe_2O_3$, $Nd_2O_3$, $La_2O_3$, $Nb_2O_5$, $Ta_2O_5$, $GeO_2$, or any other suitable metal oxide material including combinations thereof and various stoichiometric ratios thereof, according to various embodiments. In some embodiments, the MOS active material may be doped. In various embodiments, any dopant that may be useful in the construction or use of the MOS sensor may be used to dope the MOS active material. Non-limiting examples of dopants according to various embodiments may include Pt, Pd, W, Au, In, Ru, $BIn_2O_3$, or any other suitable dopant, including combinations thereof. In some embodiments, the MOS sensor array 102 may be a monolithic sensor array. In various embodiments, the gas identification engine 104 may be implemented in hardware, firmware, a field programmable gate array (FPGA), an application specific integrated circuit (ASIC), with software and one or more processors, or some combination thereof.

In some embodiments, as shown with respect to a first MOS sensor 106, some or all of the MOS sensors may include a MOS active material 108, a first electrode 110, a second electrode 112, a heater 114, and a temperature sensor 116. In various embodiments, the heater 114 and/or the temperature sensor 116 may allow monitoring and/or control of the temperature of the MOS sensor during operation. In various embodiments, each MOS sensor may have an independently controllable temperature, or subsets of the MOS sensors may have independently controllable temperatures. Although the electrodes, MOS materials, heaters, and temperature sensors are not labeled on the other MOS sensors of the MOS sensor array 102 for clarity, they may be configured in a similar fashion to that shown and described with respect to the first MOS sensor 106 in various embodiments. In some embodiments, the MOS sensors of the MOS sensor array 102 may be referred to as MOS sensor elements or pixels of the MOS sensor array 102. In accordance with some embodiments, the MOS active material 108 is shown as an outline with respect to the first MOS sensor 106 in order to illustrate the other components of the first MOS sensor 106. Although the electrodes, heaters, and temperature sensors of the other MOS sensors in the MOS sensor array 102 are partially obscured by the MOS materials, it should be understood that they may be configured in a similar fashion to that shown with respect to the first MOS sensor 106 in various embodiments. In some embodiments, the MOS sensor array 102 may include additional components not shown for clarity (e.g., conductive traces to the electrodes, heaters, and/or temperature sensors). Although the MOS sensor array 102 is shown with sixteen MOS sensors, the MOS sensor array 102 may have a different number of sensors in various embodiments.

In some embodiments, the MOS sensor array 102 may include a first column 120 having a first set of MOS sensors with a first MOS active material (e.g., $In_2O_3$), a second column 122 having a second set of MOS sensors with a second MOS active material (e.g., $SnO_2$), a third column 124 having a third set of MOS sensors with a third MOS active material (e.g., $WO_3$), and a fourth column 126 having a fourth set of MOS sensors with a fourth MOS active material (e.g., ZnO). In various embodiments, the temperature of each MOS sensor in the MOS sensor array 102 may be controlled independently of other MOS sensors in the MOS sensor array 102. In some embodiments, two or more MOS sensors in the MOS sensor array 102 may be temperature controlled together. In some embodiments, a first row 128 may be controlled to maintain a first temperature, a second row 130 may be controlled to maintain a second temperature, a third row 132 may be controlled to maintain a third temperature, and a fourth row 134 may be controlled to maintain a fourth temperature. In some embodiments, a second MOS sensor 136, belonging to the fourth column 126 and the fourth row 134, may have a MOS active material formed of the fourth MOS active material (e.g., ZnO) and be controlled to maintain the fourth temperature. In other embodiments, each MOS sensor in the MOS sensor array 102 may have an independently controllable temperature. In some embodiments, the MOS active materials of the MOS sensors may be arranged in a different manner, rather than by column, and/or each MOS sensor in the MOS sensor array may have a different MOS active material.

In some embodiments, the gas identification engine 104 may include a hybrid multi-staged machine learning model 140. In various embodiments, the hybrid multi-staged machine learning model 140 may include a plurality of regression models 142 and/or one or more artificial neural networks (ANNs) 144 employed successively in a plurality of stages in the identification of a gas and/or concentration of a gas. In various embodiments, the plurality of regression models 142 may include multiple regression models, with each regression model applying to a predetermined gas in a predetermined concentration range for MOS sensors having predetermined MOS active materials at one or more predetermined temperatures. Accordingly, more than one regression model may be used by the gas identification engine 104 when identifying a gas, estimating a concentration level of the gas, classifying the concentration of the gas into a predetermined range, and/or determining a presence of the gas. Similarly, in various embodiments, the one or more ANNs 144 may include multiple ANNs, with each ANN applying to a predetermined gas in a predetermined concentration range for MOS sensors having predetermined MOS active materials at one or more predetermined temperatures.

In some embodiments, the hybrid multi-staged machine learning model 140 may be considered to be hybrid in that more than one type of machine learning model (e.g., one or more regression models and one or more ANNs) may be used in gas presence determination, identification, concentration estimation, and/or classification into a concentration range. In some embodiments, the hybrid multi-staged machine learning model 140 may be considered to be a multi-staged in that more than one of the regression models and/or ANNs may be used sequentially in gas presence determination, identification, concentration estimation, and/or classification into a concentration range.

In some embodiments, the plurality of regression models 142 may include a first cubic multiple linear regression model 146, a second cubic multiple linear regression model 148, and/or one or more other linear regression models 150. In various embodiments, the ANNs 144 may include a first ANN 152, a second ANN 154, and/or one or more other ANNs 156, the usage of which usage is further described below with reference to FIGS. 5-9. In some embodiments, the hybrid multi-staged machine learning model 140 may include one or more other types of machine learning models (e.g., support vector machines, logistic regression algorithms, or any other suitable machine learning models), not shown for clarity. In various embodiments, the hybrid multi-staged machine learning model 140 may include logic, not shown for clarity, for combining two or more of the regression models 142, ANNs 144, or other types of machine learning models in gas presence determination, identification, concentration estimation, and/or classification into a concentration range.

In various embodiments, the gas identification engine 104 may include one or more other components 158 (e.g., processors, memory, network interfaces, and/or other components). In some embodiments, the gas identification engine 104 may include a wireless communications transceiver 160. In various embodiments, the wireless communications transceiver may communicate using one or more wireless communications standards (e.g., Institute of Electrical and Electronics Engineers (IEEE) 802.11 (Wi-Fi)). Although only the MOS sensor array 102 is shown coupled with the gas identification engine 104, it should be understood that additional MOS sensor arrays may be coupled with the gas identification engine 104 in some embodiments.

Figure 2:
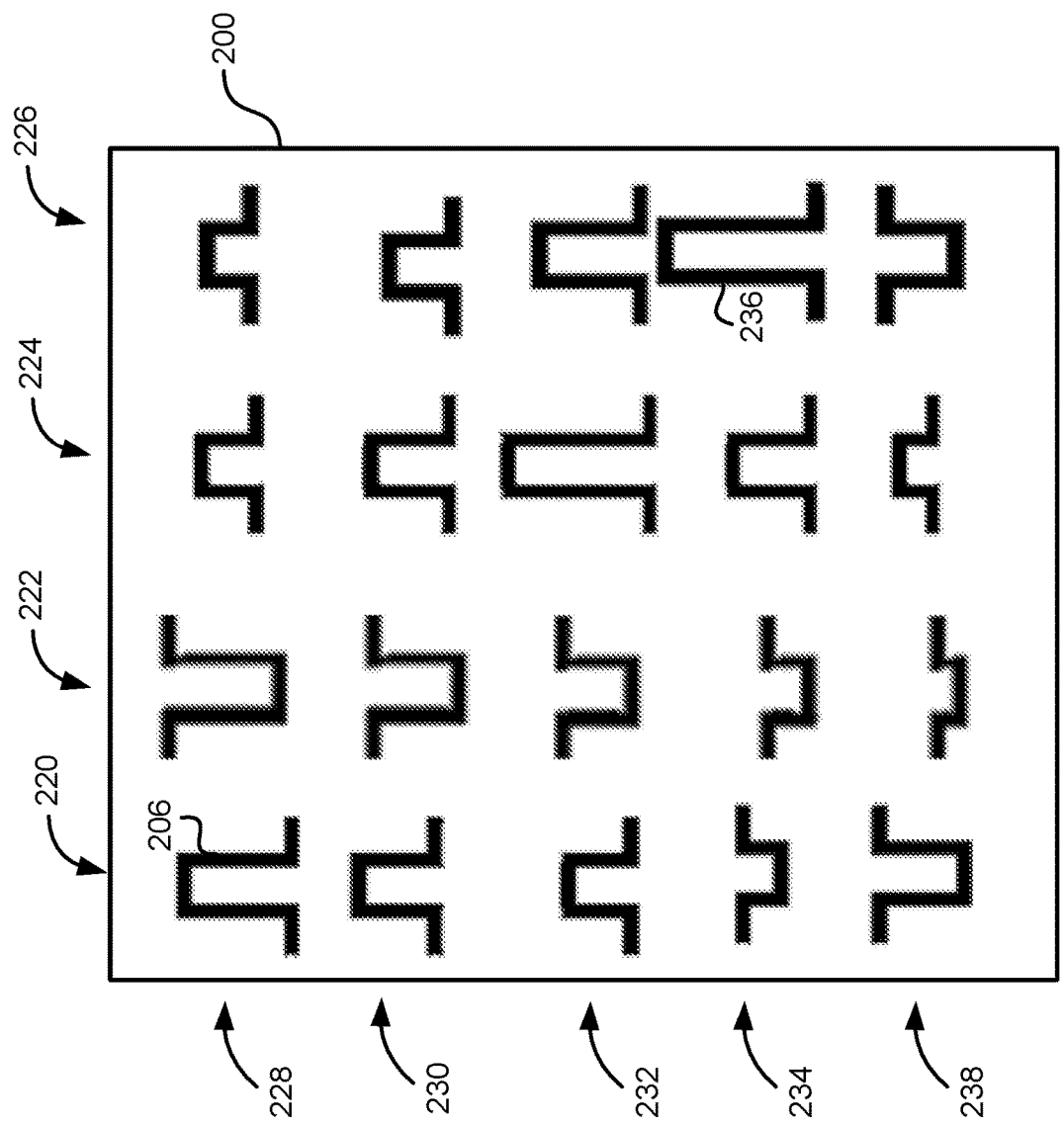
FIG. 2 is a diagram of an example response pattern of a metal oxide semiconductor array, according to various embodiments.

FIG. 2 shows a response matrix 200 with an example response pattern in accordance with various embodiments. In some embodiments, each response in the example response pattern may represent a property measurement (e.g., a resistance or a normalized resistance) of a MOS sensor element, or a change in a property measurement. In some embodiments, each response in the example response pattern may represent the property measurement over a predetermined time period during exposure to a mixture of gases. Although the response matrix 200 is shown with visual representations of pulses, it should be understood that the response matrix 200 may be represented numerically rather than visually in various embodiments.

In some embodiments, the response matrix 200 may have a response corresponding to each sensor in the MOS sensor array 102. A first pulse response 206 may correspond with the first MOS sensor 106 in various embodiments. The response matrix 200 is shown with a first column 220, a second column 222, a third column 224, and a fourth column 226, according to some embodiments. The response matrix 200 is shown with a first row 228, a second row 230, a third row 232, a fourth row 234, and a fifth row 238, in accordance with various embodiments. In some embodiments, the columns of the response matrix 200 may correspond to the columns of the MOS sensor array 102, and the first through fourth rows of the response matrix 200 may correspond to the rows of the MOS sensor array 102 such that the first pulse response 206 corresponds with the first MOS sensor 106 and a second pulse response 236 corresponds with the second MOS sensor 136. In various embodiments, the fifth row 238 of the response matrix 200 may correspond to a different MOS sensor array coupled with the gas identification engine 104, an additional row in the MOS sensor array 102, a reading from the first row 128 of the MOS sensor array 102, but taken at a different time, temperature, and/or different conditions than the pulse responses shown in row 228, a combination thereof, or any other suitable resistance response or other property measurement from one or more MOS sensors.

Figure 3:
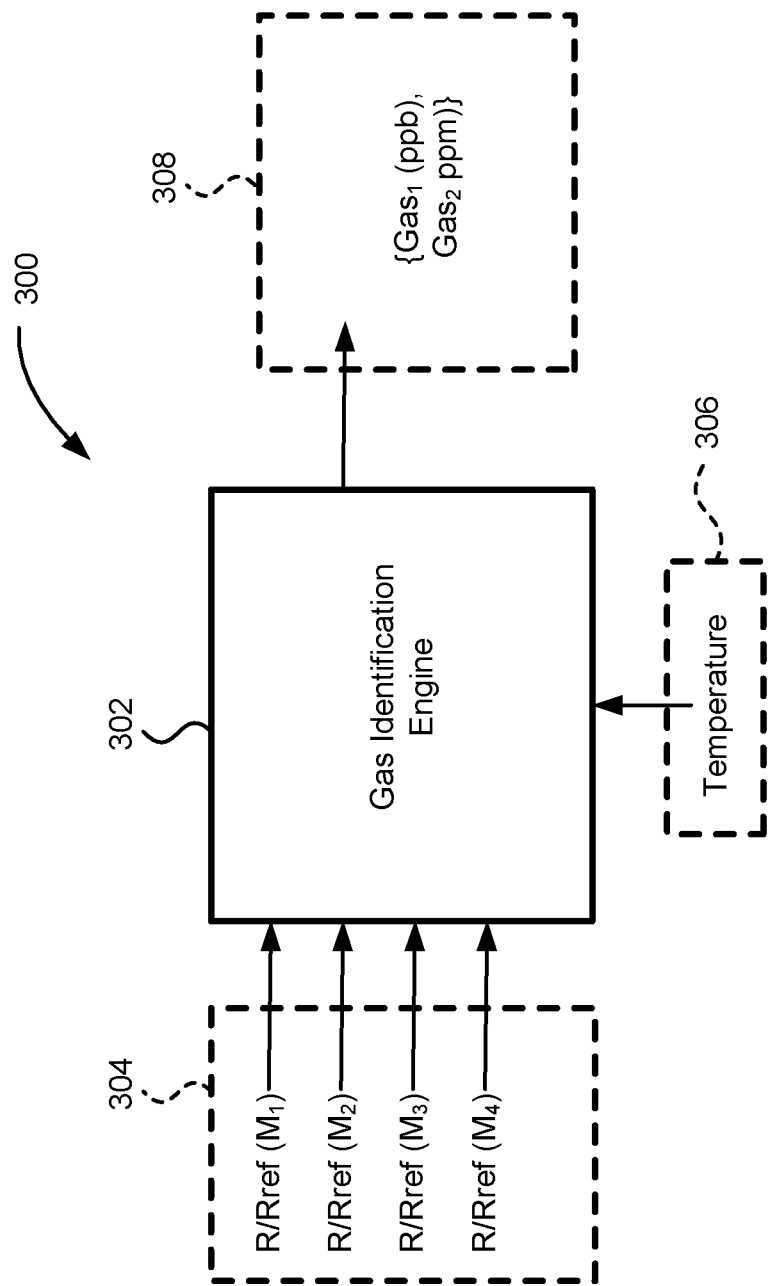
FIG. 3 is a block diagram showing a high-level view of a system for gas identification, according to various embodiments.

FIG. 3 is a block diagram showing a high-level view of a gas identification system, in accordance with some embodiments. In various embodiments, the gas identification system 300 may include a gas identification engine 302 that may include one or more of the components of the gas identification engine 104, and in particular may include the hybrid multi-staged machine-learning model 140. In some embodiments, the gas identification engine 302 may receive resistance signal inputs 304 and a temperature signal input 306 and generate an output 308 having one or more gas identification and/or gas concentration estimates based at least in part on the resistance signal inputs 304 and the temperature signal input 306.

In various embodiments, the resistance signal inputs 304 may include a plurality of normalized resistance values from a MOS sensor array (e.g., MOS sensor array 102), where the normalized resistance may be defined as the ratio of a MOS sensor resistance R for a MOS sensor having an MOS active material M in the presence of a gas mixture at a temperature T over a reference resistance for a MOS sensor having the same active MOS material at the same temperature in the presence of air only, referred to as Rref. In some embodiments, $M_1$, $M_2$, $M_3$, and $M_4$ may correspond to $In_2O_3$, $SnO_2$, $WO_3$, and ZnO, respectively. In other embodiments, one or more of the MOS active materials may be different and/or the same MOS active material may be used at different temperatures. In some embodiments, the normalized resistance input values may correspond to a mean value sensed over a predetermined detection period (e.g., 4 seconds). As shown, the resistance signal inputs may include four values, R/Rref ($M_1$), R/Rref ($M_2$), R/Rref ($M_3$), and R/Rref ($M_4$) (e.g., corresponding to resistance values from one of the four rows of sensors in the sensor array 102 and/or pulse responses in the response matrix 200). Although only four normalized resistance inputs and a single temperature input are shown, it should be understood that additional resistance inputs and/or temperature inputs may be present in various embodiments. In some embodiments, the temperature signal input 306 may include temperature data corresponding to the MOS sensors that generated the resistance signal inputs 304. For example, in various embodiments, the temperature signal input 306 may include temperature data $T_1$, $T_2$, $T_3$, and $T_4$ corresponding to temperature values of the active MOS materials $M_1$, $M_2$, $M_3$, $M_4$.

In various embodiments, the output 308 may include one or more indications of one or more gases detected by the gas identification engine 302 and/or estimated concentrations of the detected one or more gases (e.g., in parts per billion (ppb) or parts per million (ppm)). As shown, in some embodiments, the output 308 may include an indication that a first gas $Gas_1$ (e.g., $O_3$) was detected with a first estimated concentration in ppb and a second gas $Gas_2$ (e.g., CO) was detected with a second estimated concentration in ppm.

Figure 4:
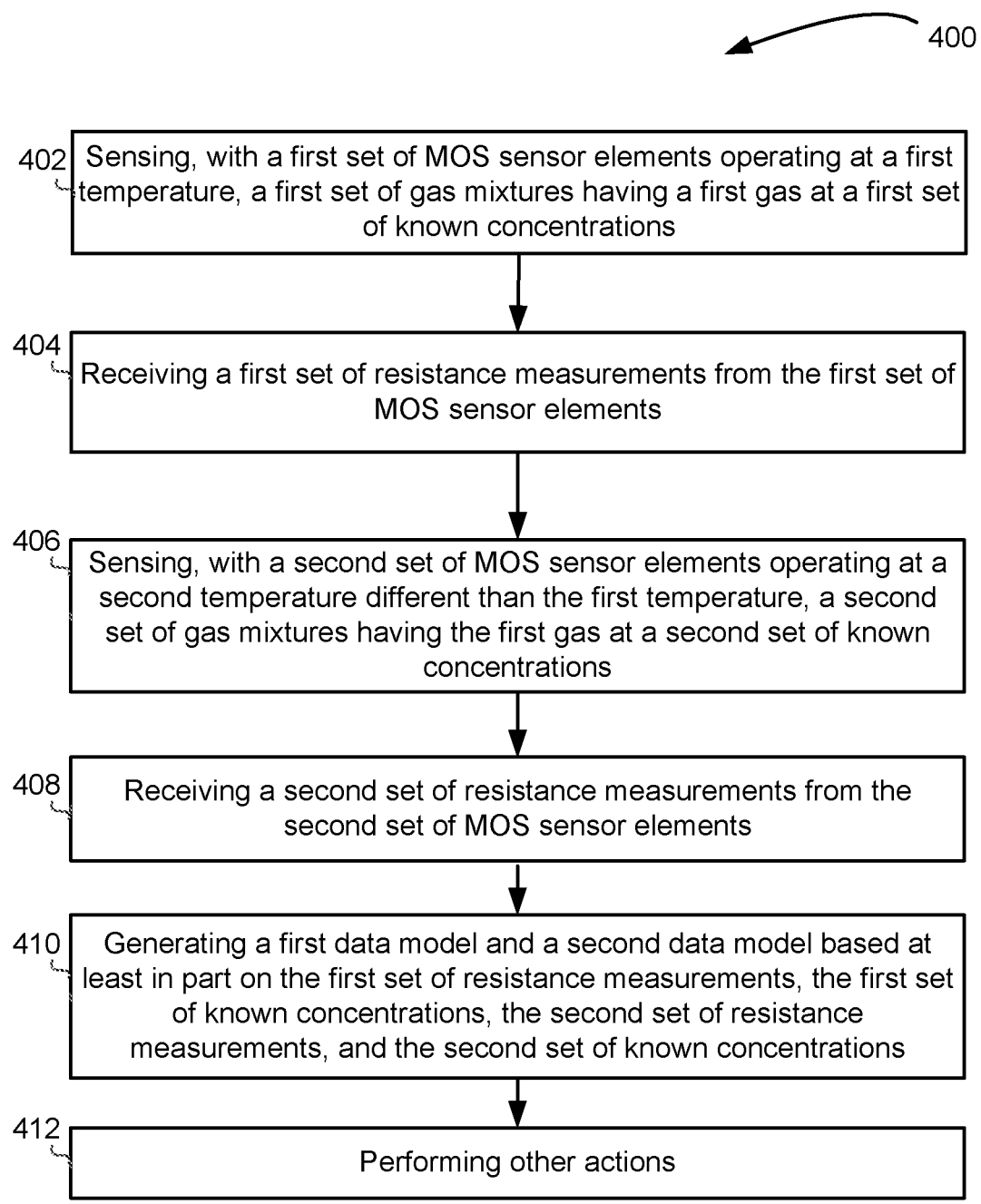
FIG. 4 is a flow diagram illustrating a method of training a hybrid multi-staged machine learning system for gas identification, according to various embodiments.

FIG. 4 is a flow diagram illustrating a method 400 of training a hybrid multi-staged machine learning system (e.g., gas identification apparatus 100) for gas identification, according to various embodiments. In some embodiments, some or all of the method 400 may be practiced by components shown and/or described with respect to the gas identification apparatus 100 of FIG. 1 and/or the system 300 of FIG. 3.

In various embodiments, the method 400 may include, at a block 402, sensing, with a first set of MOS sensor elements (e.g., MOS sensor elements in first row 128) operating at a first temperature, a first set of gas mixtures having a first gas (e.g., $O_3$ or CO) at a first set of known concentrations. In some embodiments, at a block 404, the method 400 may include receiving a first set of resistance measurements from the first set of MOS sensor elements, where the first set of resistance measurements corresponds to the sensed first set of known concentrations. For example, the first set of resistance measurements may include pulse responses of the first set of MOS sensor elements during exposure to a gas mixture having ten different known concentrations of the first gas.

In some embodiments, at a block 406, the method 400 may include sensing, with a second set of MOS sensor elements operating at a second temperature different than the first temperature, a second set of gas mixtures having the first gas at a second set of known concentrations. In some embodiments, the first set of known concentrations may be the same as the second set of known concentrations and/or sensing at the block 402 may take place simultaneously with sensing at the block 406 for each known concentration in the first and second set of known concentrations (e.g., using MOS sensors in first row 128 at the first temperature and MOS sensors in second row 130 at the second temperature). In other embodiments, the first set of known concentrations may be different than the second set of known concentrations and/or sensing at the block 402 and the block 406 may not take place simultaneously. In various embodiments, at a block 408, the method 400 may include receiving a second set of resistance measurements from the second set of MOS sensor elements, where the second set of resistance measurements corresponds to the sensed second set of known concentrations.

In some embodiments, at a block 410, the method 400 may include generating a first data model and a second data model based at least in part on the first set of resistance measurements, the first set of known concentrations, the second set of resistance measurements, and the second set of known concentrations, where the first data model fits a first concentration range of the first gas better than the second data model with respect to a first predefined fit metric, and the second data model fits a second concentration range of the first gas better than the first model with respect to a second predefined fit metric. In various embodiments, the first fit metric and/or the second fit metric may be a coefficient of multiple determination. However, it should be understood that any suitable fit metric may be used in various embodiments.

In some embodiments, the first data model may be a multiple linear regression data model and the second data model may be an artificial neural network. In various embodiments, the second data model may be a multi-staged artificial neural network and/or may include more than one artificial neural network. In other embodiments, a different type of data model (e.g., multiple regression model, artificial neural network, or any other suitable data model) may be used for the first and/or the second data model. In some embodiments, an ANN may be used as a data model only if a multiple linear regression model was first determined to not be adequate for estimating a concentration level for a particular concentration range (e.g., if a fit metric for the linear regression model is below a predetermined threshold value). In various embodiments, one or more other types of machine learning models, techniques, or algorithms (e.g., a state vector machine, a logistic regression algorithm, or any other suitable machine-learning model) may be used in addition to, or in place of using an ANN. In some embodiments, one or more of the models may be some form of classification model. In various embodiments, one or more results of a regression model, an artificial neural network, or any other model may be truncated to generate a determination of whether a gas is present in a predetermined concentration range. In some embodiments, a fit metric may be applied to the classification of whether the gas is present in the predetermined concentration range based at least in part on an error rate (e.g., a false positive rate, a false negative rate, or a combination thereof). In some embodiments, the generated data models may be temperature-dependent data models, with each data model corresponding to a single temperature of one or more MOS active materials in one or more MOS sensors.

In various embodiments, the method 400 may include performing other actions at a block 412 (e.g., generating one or more additional models, refining an existing model based at least in part on additional input, storing the generated models for later use in the hybrid multi-staged machine learning model 140, or any other suitable action). In some embodiments, the method 400 may be performed additional times to generate additional data models corresponding to other gases. In some embodiments, the method 400 may be performed with one or more additional gases at known concentrations to generate data models for more than one gas concurrently, and/or for gas combinations that may potentially interfere with each other during sensing and measurement (e.g., a first gas having a reducing effect on the MOS sensors and a second gas having an oxidizing effect). In some embodiments, the method 400 may be performed with both $O_3$ and CO present in the gas mixtures at known concentrations when the gas mixtures are sensed at the blocks 402 and 406.

In various embodiments, the method 400 may be iteratively performed at multiple temperatures to optimize the specific temperature thresholds used for each gas to identify the best concentration ranges and temperatures that correspond to an optimized set of data models that are generated and stored in the hybrid multi-staged machine learning model 140. In some embodiments, generating the data models at the block 410 may include generating logic to combine the data models in a hybrid and/or multi-staged approach. For example, in some embodiments, generating the data models at the block 410 may include: generating a first data model using resistance data collected at a first temperature, where the first data model establishes whether a gas is present above a particular decision boundary; generating a second data model using resistance data collected at a second temperature to be used for concentrations less than or equal to the decision boundary; generating a third data model using resistance data collected at a third temperature to be used for concentrations greater than the decision boundary; and generating logic to combine the generated data models. In various embodiments, the generated logic and data models may later be used for detection, identification, classification, and/or concentration estimation of particular gases (e.g., as described with respect to FIGS. 5-9).

Figure 5:
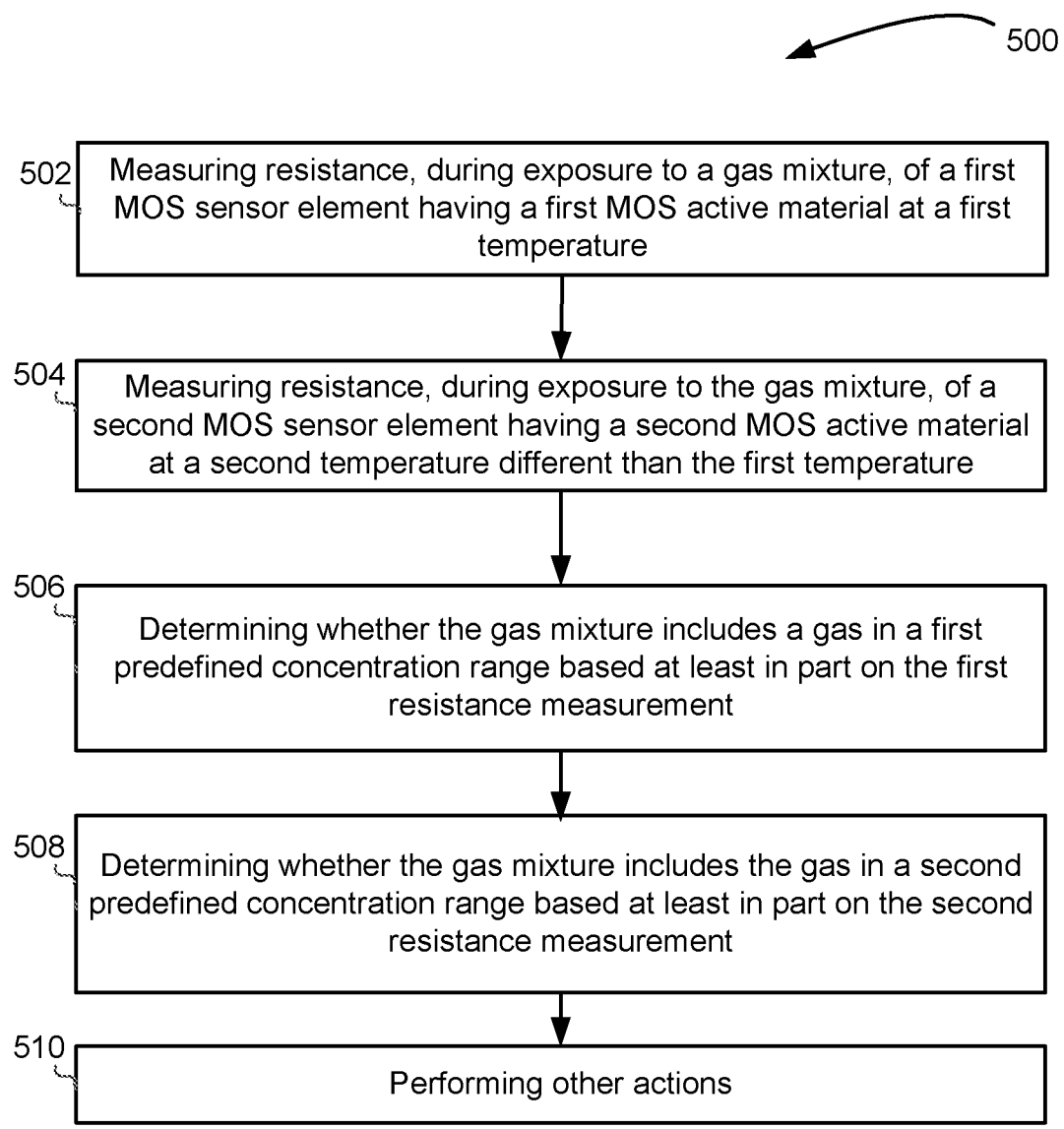
FIG. 5 is a flow diagram illustrating a method of identifying a gas using a hybrid multi-staged machine learning system, according to various embodiments.

FIG. 5 is a flow diagram illustrating a method 500 of identifying a gas using a hybrid multi-staged machine learning system, according to various embodiments. In some embodiments, at a block 502, the method 500 may include measuring resistance, during exposure to a gas mixture, of a first MOS sensor element (e.g., first MOS sensor element 106) operating with a first MOS active material at a first temperature to produce a first resistance measurement. In various embodiments, at a block 504, the method 500 may include measuring resistance, during exposure to the gas mixture, of a second MOS sensor element (e.g., second MOS sensor element 136) operating with a second MOS active material at a second temperature different than the first temperature to produce a second resistance measurement. In some embodiments, the first resistance measurement and/or the second resistance measurement may be normalized resistance measurements and/or may be a mean value of resistance measurements taken over a predetermined time period (e.g., such as described with respect to the system 300 of FIG. 3).

In some embodiments, measuring resistance at the block 502 to produce the first resistance measurement and measuring resistance at the block 504 to produce the second resistance measurement may take place simultaneously. In other embodiments, measuring resistance at the block 502 and measuring resistance at the block 504 may take place at different times. In some embodiments where the measurements are taken at different times, the first MOS sensor element and the second MOS sensor element may be the same MOS sensor element (e.g., first MOS sensor element 106), but having a first temperature (e.g., 200 degrees Celsius) when resistance is measured at the block 502, and a second temperature (e.g., 300 degrees Celsius) when resistance is measured at the block 504.

In various embodiments, at a block 506, the method 500 may include determining whether the gas mixture includes a gas in a first predefined concentration range based at least in part on the first resistance measurement (e.g., with one or more of the regression models 142 or ANNs 144 in the hybrid multi-staged machine learning model 140). At a block 508, in some embodiments, the method 500 may include determining whether the gas mixture includes the gas in a second predefined concentration range based at least in part on the second resistance measurement (e.g., with one or more of the regression models 142 or ANNs 144 in the hybrid multi-staged machine learning model 140). In some embodiments, determining whether the gas mixture includes the gas in the first predefined concentration range and/or in the second predefined concentration range may be performed with a classification model (e.g., by using a truncated result of a regression model or an ANN). In various embodiments, at a block 510, the method 500 may include performing other actions (e.g. generating an alert if the gas exceeds a predefined threshold, sending one or more determinations to a monitoring system, determining whether the gas mixture includes the gas in additional predefined concentration ranges, and/or any other suitable action).

In some embodiments, determining whether the gas mixture includes the gas in the first predefined concentration range at the block 506 may be based at least in part on one or more additional resistance measurements of one or more other MOS sensor elements having MOS active materials at the first temperature. In some embodiments, determining whether the gas mixture includes the gas in the second predefined concentration range at the block 508 may be based at least in part on one or more additional resistance measurements of one or more other MOS sensor elements having MOS active materials at the second temperature. In some embodiments, determining whether the gas mixture includes the gas in the first predefined concentration range at the block 506 may be based at least in part on resistance measurements from MOS sensor elements having MOS active materials at more than one temperature. In some embodiments, determining whether the gas mixture includes the gas in the second predefined concentration range at the block 508 may be based at least in part on resistance measurements from MOS sensor elements having MOS active materials at more than one temperature.

Figure 6:
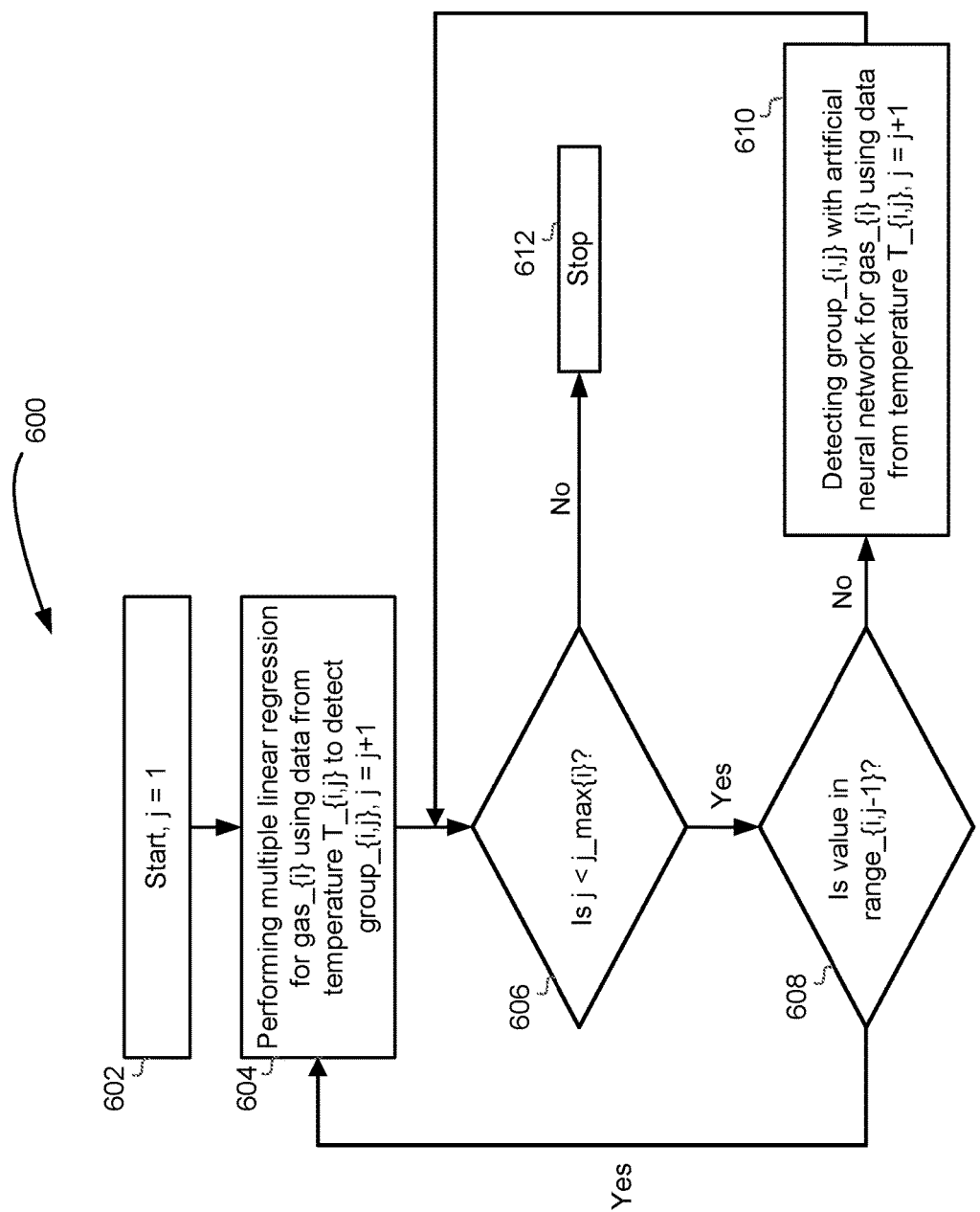
FIG. 6 is a flow diagram illustrating a flow diagram illustrating a gas classification method using a hybrid multi-staged machine learning system, according to various embodiments.

FIG. 6 is a flow diagram illustrating a flow diagram illustrating a gas classification method 600 using a hybrid multi-staged machine learning system, including an algorithm for a multi-pass classification, according to various embodiments. In some embodiments, the method 600 may start at a block 602 where a counting variable, 'j', may be set to one. In some embodiments, the method 600 may be performed for a maximum number of steps j_max{i} that may correspond to a number of passes that may be performed by a classification algorithm, where a particular gas may be associated with a predetermined value of 'i' (e.g., $O_3$ for i=1, CO for i=2) and the value of j_max{i} may be different for each gas. In various embodiments, at a block 604, the method 600 may include performing multiple linear regression for a gas designated as gas_{i}. In some embodiments, the multiple linear regression may be performed with resistance measurement data from a temperature designated at T_{i,j} where a predetermined temperature may be associated with each pass, 'j', of the multi-pass classification algorithm for each gas, 'i'. In some embodiments, the multiple linear regression may be performed to detect whether the gas_{i} is in a group_{i, j}, where group_{i, j} may correspond to a group of concentration values or a concentration range for the current pass of the algorithm 'j' and gas 'i'. In various embodiments, the counting variable, T may be incremented with j=j+1. In some embodiments, at a decision block 606, the method 600 may include determining whether the counting variable, 'j', is less than the maximum number of passes in the multi-pass classification algorithm for a particular gas, 'i'. In some embodiments, detecting whether the gas_{i} is in the group_{i, j} may be performed using a classification data model (e.g., by truncating a result of a multiple linear regression data mode).

If, at the decision block 606, it is determined that j<j_max{i}, the method 600 may include determining whether an estimated concentration value of the gas {i} is in a predetermined range_{i, j−1} at a decision block 608. If, at the decision block 608, it is determined the estimated concentration value of the gas is not in range_{i, j−1}, the method 600 may, at a block 610, include detecting group {i, j} with an ANN for gas_{i} using data from temperature T_{i, j}. In some embodiments, the counting variable, 'j', may be incremented with j=j+1. In some embodiments, the method 600 may then proceed back to the decision block 606. If, at the decision block 608, it is determined the estimated concentration value of the gas is in range_{i, j−1}, the method 600 may proceed back to the block 604.

In some embodiments, if, at the decision block 606, it is determined that 'j' is not less than j_max{i}, the method may proceed to a block 612 where the method 600 may stop. In various embodiments, one or more additional actions, not shown for clarity, may be performed such as storing one or more estimated gas concentrations, gas presence determinations, or gas concentration range classifications, and/or transmitting one or more determinations to a monitoring system. In some embodiments, the number of passes through the method 600 may be customizable and/or some passes may correspond to progressively higher resolution ranges.

Figure 7:
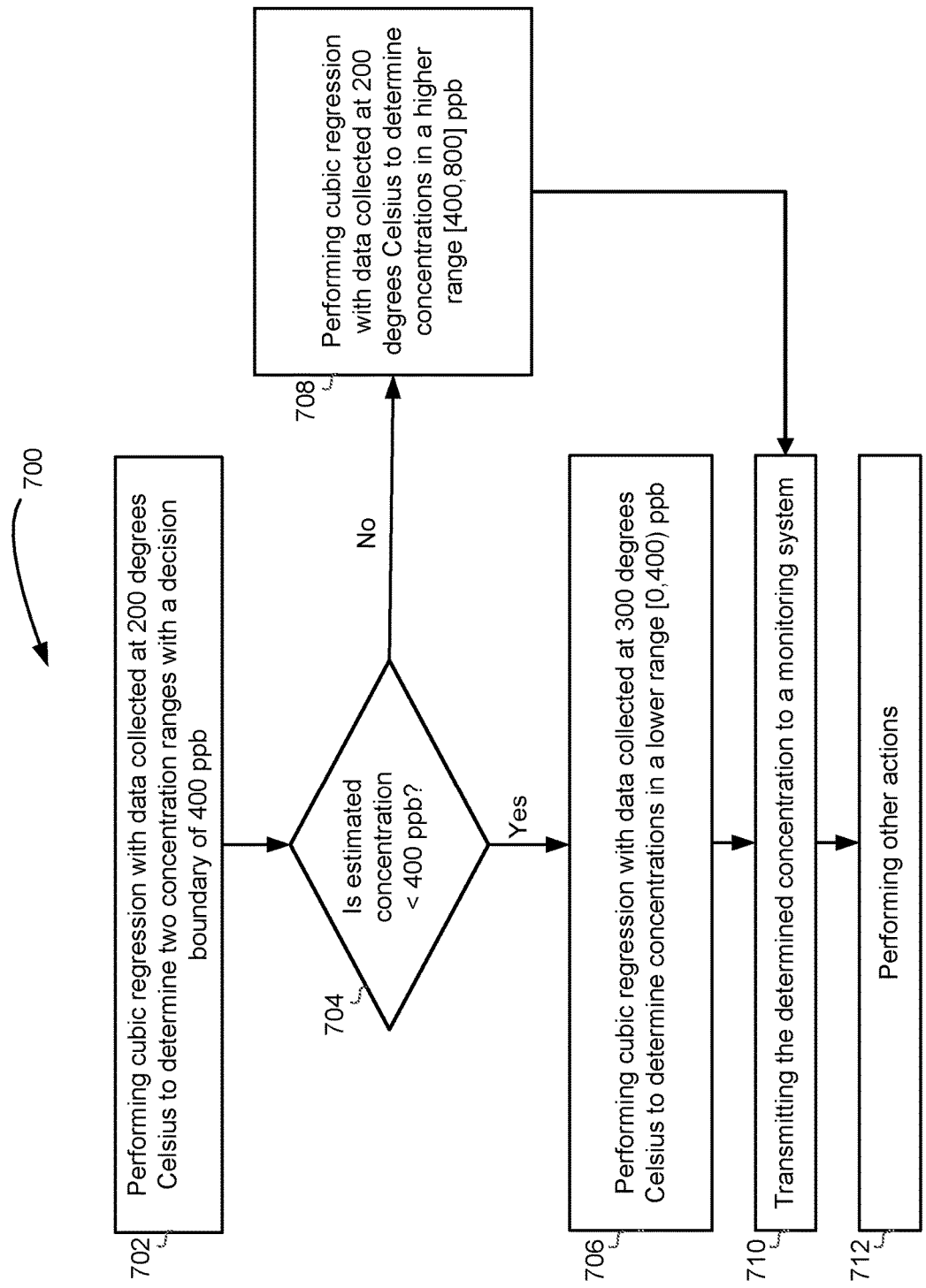
FIG. 7 is a flow diagram illustrating a method of identifying a concentration of a gas using a hybrid multi-staged machine learning system, according to various embodiments.

FIG. 7 is a flow diagram illustrating a method of identifying a concentration of a gas using a hybrid multi-staged machine learning system, according to various embodiments. In some embodiments, the method 700 may relate to identifying a concentration of $O_3$ in a gas mixture, but it should be understood that the method 700 is not limited with respect to the type of gas detected, the particular temperatures mentioned, or the particular concentrations mentioned as an example to illustrate the principles of the method 700. In some embodiments, at a block 702, the method 700 may include performing cubic regression with data collected at 200 degrees Celsius to determine two concentration ranges with a decision boundary of 400 ppb (e.g., with one of the regression models 142). In some embodiments, at a decision block 704, the method 700 may include determining whether the estimated concentration is less than 400 ppb based at least in part on the cubic regression performed at the block 702. If, at the decision block 704, it is determined the estimated concentration is less than 400 ppb, the method 700 may include performing cubic regression with data collected at 300 degrees Celsius to determine estimated concentrations in a lower range greater than or equal to zero and less than 400 ppb ([0,400) ppb) (e.g., with one of the regression models 142). If, at the decision block 704, it is determined the estimated concentration is not less than 400 ppb, the method 700 may include performing cubic regression with data collected at 200 degrees Celsius to determine concentrations in a higher range greater than or equal to 400 and less than or equal to 800 ppb ([400,800] ppb) (e.g., with one of the regression models 142).

In some embodiments, the method 700 may include transmitting the determined concentration to a monitoring system at a block 710 (e.g., with the wireless communications transceiver 160). In various embodiments, the method 700 may include performing other actions at a block 712.

Figure 8:
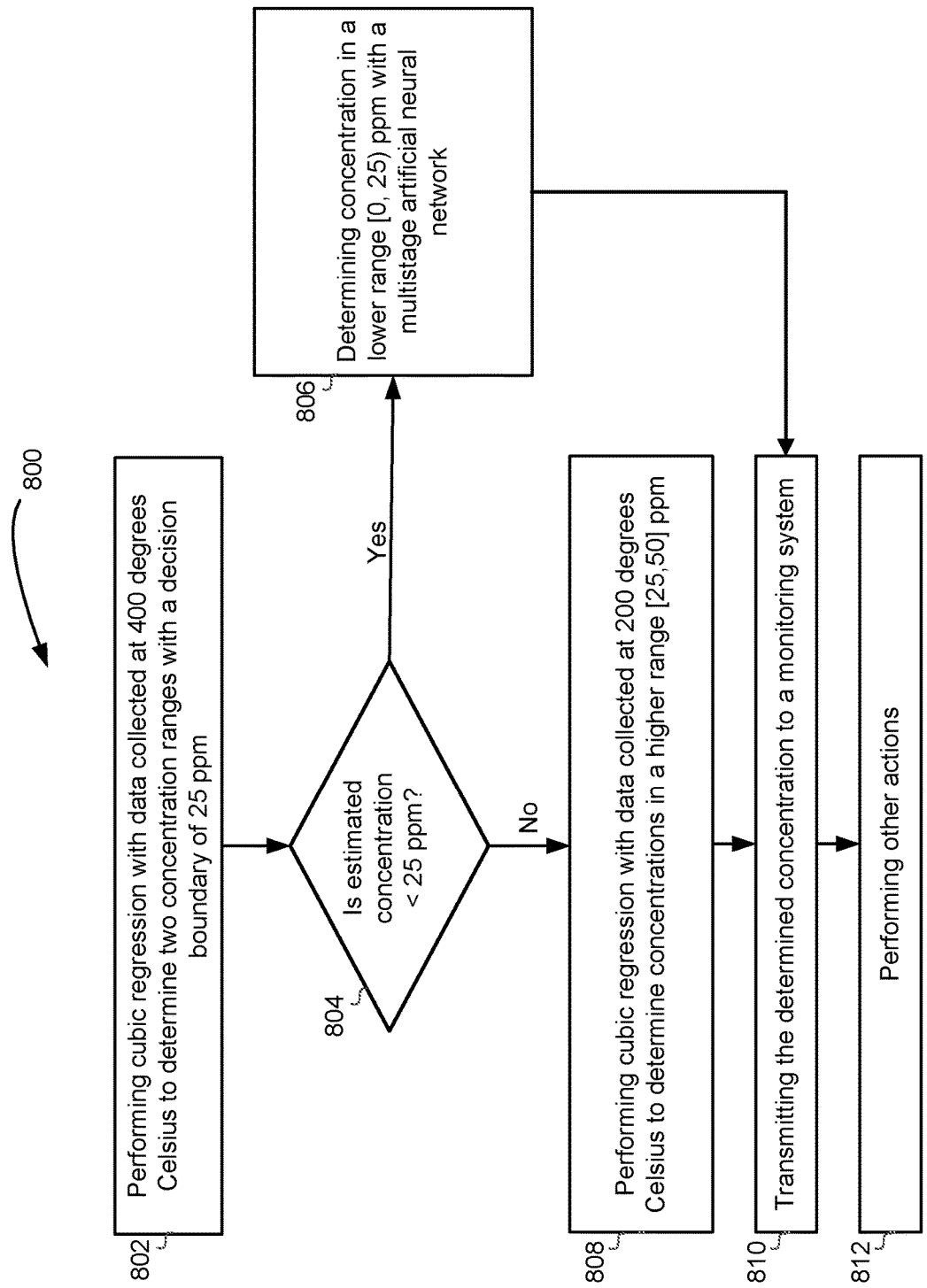
FIG. 8 is a flow diagram illustrating a method of detecting a concentration of a gas using a hybrid multi-staged machine learning system, according to various embodiments.

FIG. 8 is a flow diagram illustrating a method 800 of detecting a concentration of a gas in a gas mixture using a hybrid multi-staged machine learning system, according to various embodiments. In some embodiments, the gas may be carbon monoxide (CO), but it should be understood that the method 800 is not limited with respect to the type of gas detected, the particular temperatures mentioned, or the particular concentrations mentioned as an example to illustrate the principles of the method 800. In some embodiments, at a block 802, the method 800 may include performing cubic regression with data collected at 400 degrees Celsius to determine two concentration ranges with a decision boundary of 25 ppm (e.g., with one of the regression models 142). In various embodiments, at a decision block 804, the method 800 may include determining whether the estimated concentration is less than 25 ppm based at least in part on the cubic regression performed at the block 802. If, at the decision block 804, it is determined the estimated concentration is less than 25 ppm, the method 800 may include, at a block 806, determining concentration in a lower range greater than or equal to zero and less than 25 ppm ([0,25] ppm) with a multistage artificial neural network (e.g., with one or more of the ANNs 144). If, at the decision block 804, it is determined the estimated concentration is not less than 25 ppm, the method 800 may include performing cubic regression with data collected at 200 degrees Celsius to determine concentrations in a higher range greater than or equal to 25 and less than or equal to 50 ppm ([25, 50] ppm) (e.g., with one of the regression models 142). In some embodiments, the method 800 may include transmitting the determined concentration from the block 806 or the block 808 to a monitoring system at a block 810 (e.g., with wireless communications transceiver 160). In various embodiments, the method 800 may include performing other actions at a block 812.

Figure 9:
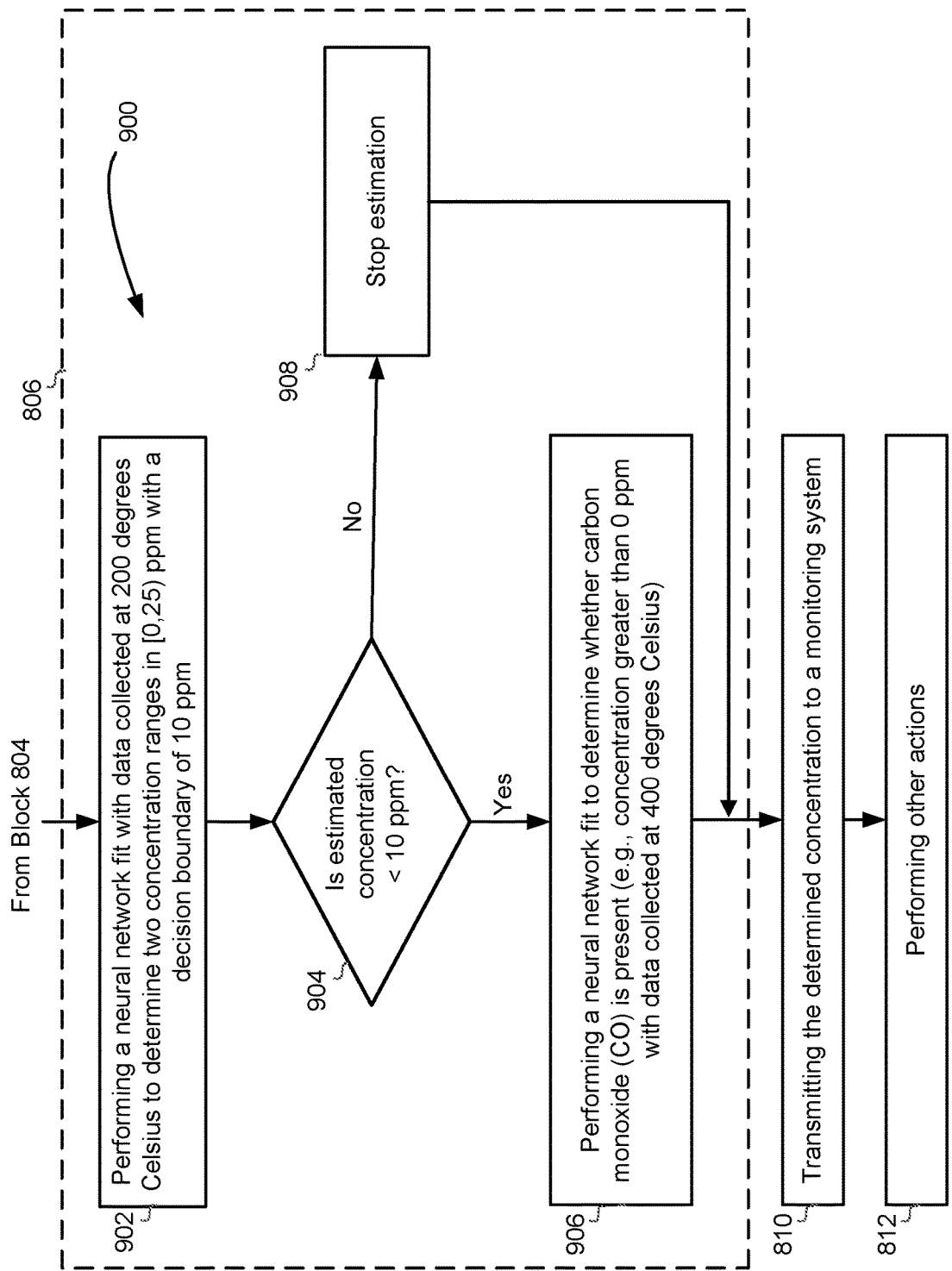
FIG. 9 is a flow diagram illustrating a second stage of a method of detecting a concentration of a gas using a hybrid multi-staged machine learning system, according to various embodiments.

FIG. 9 is a flow diagram illustrating a second stage of the method 800 of detecting a concentration of a gas, according to various embodiments. A mentioned above with respect to the method 800, it should be understood that the second stage 900 is not limited with respect to the type of gas detected, the particular temperatures mentioned, or the particular concentrations mentioned as an example to illustrate the principles of the second stage 900. In some embodiments, the second stage 900 may include one or more actions performed with respect to the block 806 of the method 800, as shown. In some embodiments, the second stage 900 may include, at a block 902, performing a neural network fit with data collected at 200 degrees Celsius to determine two concentration ranges having a decision boundary of 10 ppm within the lower range determined at the decision block 804 of greater than or equal to zero and less than 25 ppm (e.g., with one or more ANNs 144 in the hybrid multi-staged machine learning model 140).

In some embodiments, at a decision block 904, the second stage 900 may include determining whether the estimated concentration is less than 10 ppm based at least in part on the neural network fit performed at the block 902. If, at the decision block 904, it is determined the estimated concentration is less than 10 ppm, the second stage 900 may include performing a neural network fit to determine whether CO is present (e.g., with a concentration greater than 0 ppm). In some embodiments, the neural network fit performed at the block 906 may be performed with data collected at 400 degrees Celsius. If, at the decision block 904, it is determined the estimated concentration is not less than 10 ppm, the second stage 900 may stop performing further concentration estimations at a block 908, in various embodiments. Since it had been previously determined that the gas was present in the concentration range [0, 25) ppm, and at the decision block 904 it was determined the estimated concentration of the gas is not less than 10 ppm using the neural network fit from the block 902, the gas would be in the concentration range greater than or equal to 10 ppm and less than 25 ppm ([10, 25) ppm) if the block 908 is reached in the second stage 900. In some embodiments, the method 800 may include transmitting the determined range of [10, 25) ppm at the block 810 after further estimation is stopped at the block 908. In various embodiments, performing the neural network fit at the block 906 may include estimating a concentration if CO is determined to be present. In other embodiments, performing the neural network fit at the block 906 may include a binary presence indicator, indicating whether CO is determined to be present, without further estimation of gas concentration. In some embodiments, the presence indicator, a range, or a classification indicator may be transmitted at the block 810 rather than the determined concentration.

In some embodiments, components and/or methods described with respect to FIGS. 1-9, such as the gas identification apparatus 100, including the gas identification engine 104, the system 300, the method 400, the method 500, the method 600, the method 700, the method 800, the method 900, and/or other components or methods may be used to simultaneously detect, identify, classify, perform a concentration estimation, or perform any other suitable action with respect to more than one analyte (e.g., more than one gas) in an operating environment (e.g., ambient air quality monitoring or factory exhaust). In some embodiments, components and/or methods described with respect to FIGS. 1-9, such as the gas identification apparatus 100, including the gas identification engine 104, the system 300, the method 400, the method 500, the method 600, the method 700, the method 800, the method 900, and/or other components or methods may: generate and/or use one or more classification models generated by mapping truncated results of a regression model to a corresponding classification model; generate and/or use multi-staged models that use a constant single temperature for each stage; generate and/or use ANN models or other non-linear models only when a linear regression model is determined to not adequately meet a predefined metric; and/or use any other suitable technique to reduce computational complexity and/or hardware requirements that in some embodiments may reduce cost, power demand, processing time, size, and/or other aspects that may allow the components to more easily be incorporated in some systems (e.g., miniaturized, dense wireless sensor networks).

Figure 10:
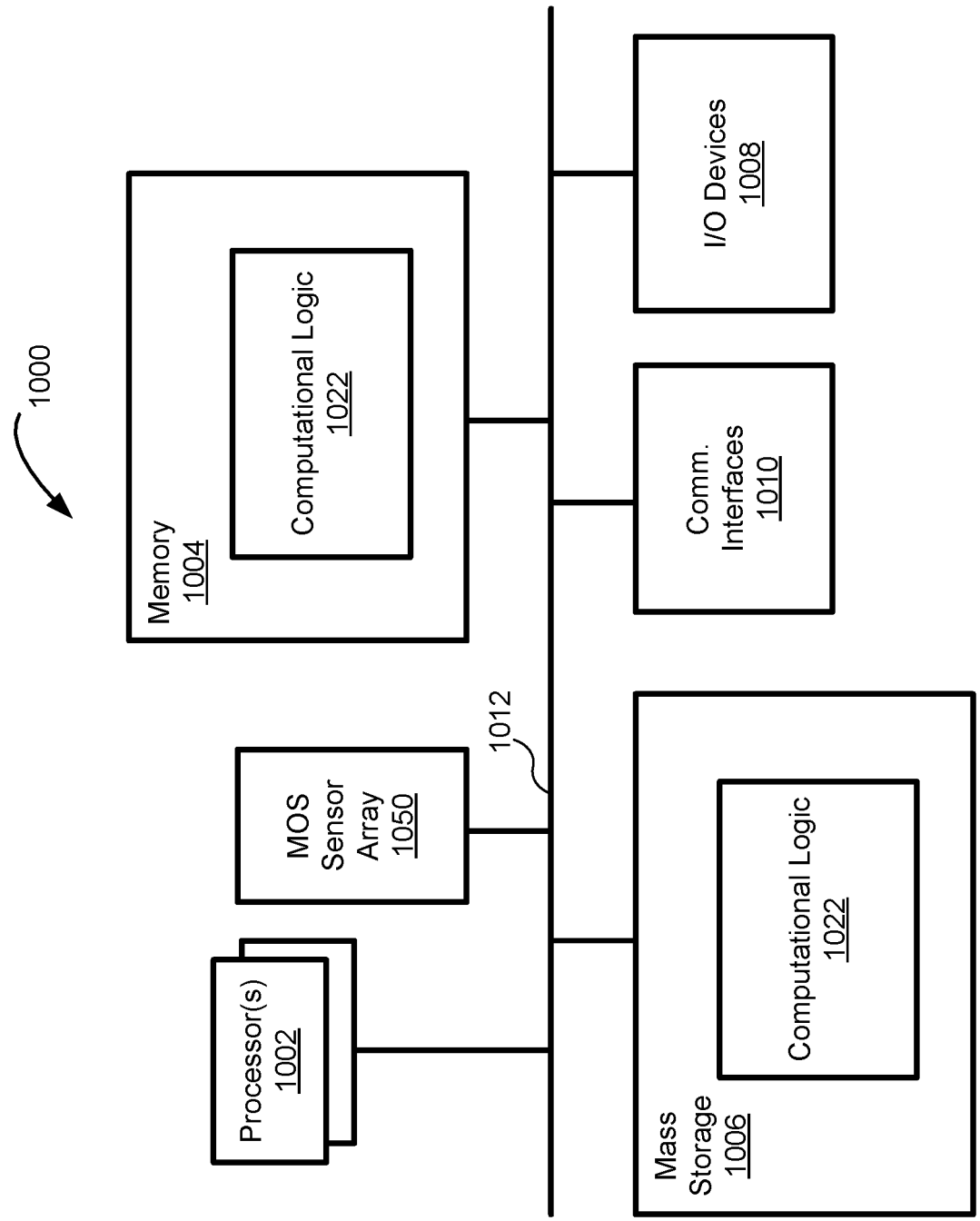
FIG. 10 schematically illustrates an example computer device to be used in gas identification using a hybrid multi-staged machine learning system, according to various embodiments.

FIG. 10 illustrates an example computer device 1000 that may include components corresponding to and/or implementing various components and methods of FIGS. 1-9, such as gas identification apparatus 100 with gas identification engine 104, described with respect to FIG. 1, in accordance with various embodiments. As shown, computer device 1000 may include one or more processors 1002, each having one or more processor cores, and system memory 1004. The processor 1002 may include any type of processors, and may include single or multi-core microprocessors, and the like. The processor 1002 may be implemented as an integrated circuit. The computer device 1000 may include mass storage devices 1006 (such as diskette, hard drive, volatile memory (e.g., dynamic random-access memory (DRAM), compact disc read-only memory (CD-ROM), digital versatile disk (DVD), and so forth). In general, system memory 1004 and/or mass storage devices 1006 may be temporal and/or persistent storage of any type, including, but not limited to, volatile and non-volatile memory, optical, magnetic, and/or solid state mass storage, and so forth. Volatile memory may include, but is not limited to, static and/or dynamic random access memory. Non-volatile memory may include, but is not limited to, electrically erasable programmable read-only memory, phase change memory, resistive memory, and so forth.

The computer device 1000 may further include input/output devices 1008 (such as a display (e.g., a touchscreen display), keyboard, cursor control, remote control, gaming controller, image capture device, and so forth) and communication interfaces 1010 (such as network interface cards, modems, infrared receivers, radio receivers (e.g., Bluetooth), and so forth).

The communication interfaces 1010 may include communication chips (not shown) that may be configured to operate the computer device 1000 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 1010 may operate in accordance with other wireless protocols in other embodiments.

The above-described computer device 1000 elements may be coupled to each other via system bus 1012, which may represent one or more buses. In the case of multiple buses, they may be bridged by one or more bus bridges (not shown). Each of these elements may perform its conventional functions known in the art. In particular, system memory 1004 and mass storage devices 1006 may be employed to store a working copy and a permanent copy of the programming instructions, such as drivers, for the operation of various components of computer device 1000, including but not limited to operation of the gas identification apparatus 100, including the gas identification engine 104 of FIG. 1, an operating system of computer device 1000, MOS sensor array 1050, and/or one or more applications, collectively referred to as computational logic 1022. The various elements may be implemented by assembler instructions supported by processor(s) 1002 or high-level languages that may be compiled into such instructions. In some embodiments, the MOS sensor array 1050 may correspond to the MOS sensor array 102 described with respect to FIG. 1.

Although the MOS sensor array 1050 is shown to be coupled with components of the computing device 1000 via system bus 1012, in other embodiments, the MOS sensor array 1050 may be in data communication with one or more components of the computing device 1000, but may be remote from the components of the computing device 1000, which may receive data from the MOS sensor array 1050 over a wireless or a wired network. In various embodiments, one or more elements of the computing device 1000 may be hosted on and/or configured as a cloud computing system or device (e.g., one or more cloud computing servers) that may receive data from the MOS sensor array 1050 and/or perform one or more actions described with respect to the gas identification engine 104 of FIG. 1 and/or the methods described with respect to FIGS. 4-9. In some embodiments, one or more elements of the computing device 1000 may be included in and/or configured as a gateway device (e.g., a mobile phone, a tablet, a laptop, or any other suitable device) that may receive data from the MOS sensor array 1050 and/or perform one or more actions described with respect to the gas identification engine 104 of FIG. 1 and/or the methods described with respect to FIGS. 4-9.

The permanent copy of the programming instructions may be placed into mass storage devices 1006 in the factory or in the field through, for example, a distribution medium (not shown), such as a compact disc (CD), or through communication interface 1010 (from a distribution server (not shown)). That is, one or more distribution media having an implementation of the agent program may be employed to distribute the agent and to program various computing devices.

The number, capability, and/or capacity of the elements 1008, 1010, 1012 may vary, depending on whether computer device 1000 is used as a stationary computing device, such as a set-top box or desktop computer, or a mobile computing device, such as a tablet computing device, laptop computer, game console, or smartphone. Their constitutions are otherwise known, and accordingly will not be further described.

For some embodiments, at least one of processors 1002 may be packaged together with a storage medium having all or portions of computational logic 1022 configured to facilitate aspects of embodiments described herein to form a System in Package (SiP) or a System on Chip (SoC).

The computer device 1000 may include or otherwise be associated with an gas identification system or apparatus that may include components and/or implement methods described with respect to FIGS. 1-9, such as the gas identification apparatus 100, including the gas identification engine 104, the system 300, the method 400, the method 500, the method 600, the method 700, the method 800, the method 900, and/or other components or methods in accordance with various embodiments. In some embodiments, one or more components such as processor 1002 may be included as a part of the gas identification apparatus 100 such as the gas identification engine 104.

In various implementations, the computer device 1000 may comprise one or more components of a data center, a laptop, a netbook, a notebook, an ultrabook, a smartphone, a tablet, a personal digital assistant (PDA), an ultra mobile PC, a mobile phone, or a digital camera. In further implementations, the computer device 1000 may be any other electronic device that processes data.

Figure 11:
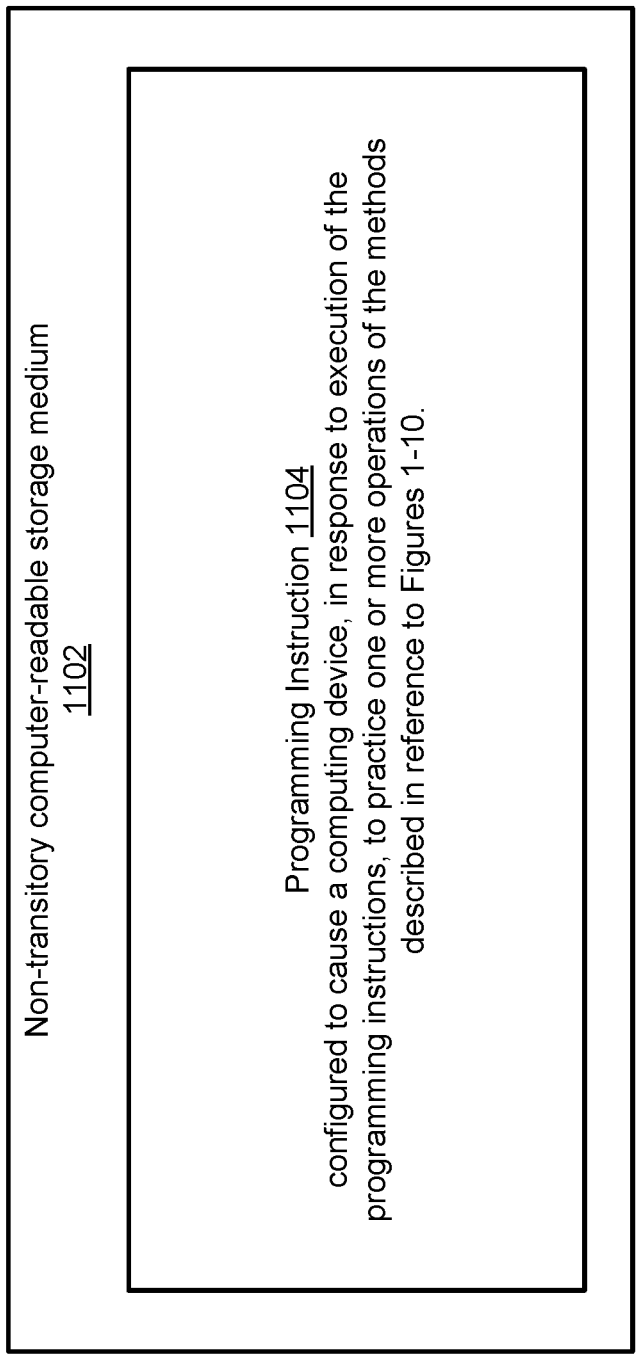
FIG. 11 illustrates an example storage medium with instructions configured to enable an apparatus to practice various aspects of the present disclosure, in accordance with various embodiments.

FIG. 11 illustrates example computer-readable storage medium 1102 having instructions configured to practice all or selected ones of the operations associated with the computer device 1000, MOS sensor array 1050, earlier described with respect to FIG. 10; the gas identification apparatus 100 including the gas identification engine 104 of FIG. 1; the system 300 described with respect to FIG. 3; and/or one or more of the methods 400, 500, 600, 700, 800, and/or 900 described with respect to FIGS. 4-9, in accordance with various embodiments. As illustrated, computer-readable storage medium 1102 may include a number of programming instructions 1104. The storage medium 1102 may represent a broad range of non-transitory persistent storage medium known in the art, including but not limited to flash memory, dynamic random access memory, static random access memory, an optical disk, a magnetic disk, etc. Programming instructions 1104 may be configured to enable a device, e.g., computer 1000 and/or gas identification engine 104 of FIG. 1, in response to execution of the programming instructions 1104, to perform, e.g., but not limited to, various operations described for the gas identification engine 104, and/or other components of FIG. 1, or operations shown in system 300 of FIG. 3, and/or one or more of the methods 400, 500, 600, 700, 800, and/or 900 described with respect to FIGS. 4-9. In alternate embodiments, programming instructions 1104 may be disposed on multiple computer-readable storage media 1102. In alternate embodiments, storage medium 1102 may be transitory, e.g., signals encoded with programming instructions 1104.

Referring back to FIG. 10, for an embodiment, at least one of processors 1002 may be packaged together with memory having all or portions of computational logic 1022 configured to practice aspects described for the gas identification engine 104, and/or other components of FIG. 1, or operations shown in system 300 of FIG. 3, and/or one or more of the methods 400, 500, 600, 700, 800, and/or 900 described with respect to FIGS. 4-9. For an embodiment, at least one of processors 1002 may be packaged together with memory having all or portions of computational logic 1022 configured to practice aspects described for the gas identification engine 104, and/or other components of FIG. 1, or operations shown in system 300 of FIG. 3, and/or one or more of the methods 400, 500, 600, 700, 800, and/or 900 described with respect to FIGS. 4-9 to form a System in Package (SiP). For an embodiment, at least one of processors 1002 may be integrated on the same die with memory having all or portions of computational logic 1022 configured to practice aspects described for the gas identification engine 104, and/or other components of FIG. 1, or operations shown in system 300 of FIG. 3, and/or one or more of the methods 400, 500, 600, 700, 800, and/or 900 described with respect to FIGS. 4-9. For an embodiment, at least one of processors 1002 may be packaged together with memory having all or portions of computational logic 1022 configured to practice aspects of the gas identification engine 104, and/or other components of FIG. 1, or operations shown in system 300 of FIG. 3, and/or one or more of the methods 400, 500, 600, 700, 800, and/or 900 described with respect to FIGS. 4-9 to form a System on Chip (SoC). For at least one embodiment, the SoC may be utilized in, e.g., but not limited to, a mobile computing device such as a wearable device, an internet of things (IoT) device, and/or a smartphone.

As discussed above in relation to the gas identification apparatus 100 described with respect to FIG. 1, it should be understood that the devices, systems, methods, and/or other aspects shown and described with respect to FIGS. 2-11 may be used to perform detection, identification, estimation of concentration level, or classification into concentration ranges of one or more analytes that may not be gases (e.g., airborne inorganic molecules, airborne organic molecules, airborne particulate matter, or any other analyte for which detection is sought, including combinations thereof).

Machine-readable media (including non-transitory machine-readable media, such as machine-readable storage media), methods, systems and devices for performing the above-described techniques are illustrative examples of embodiments disclosed herein. Additionally, other devices in the above-described interactions may be configured to perform various disclosed techniques.

EXAMPLES

Example 1 may include a gas identification apparatus, comprising: a set of heterogeneous metal oxide semiconductor (MOS) sensors to provide different response patterns for the presence of different gases; and an identification engine coupled with the sensors, and having a plurality of regression models and one or more artificial neural networks, to analyze a response pattern to identify presence of a gas, based at least in part on a plurality of property measurements of the MOS sensors when exhibiting the response pattern, and using one or more of the plurality of regression models and the one or more artificial neural networks.

Example 2 may include the subject matter of Example 1, wherein the identification engine is to determine whether the gas is present in a first predefined concentration range based at least in part on a plurality of resistance measurements from the sensors using one or more of a multiple linear regression model and the one or more artificial neural networks.

Example 3 may include the subject matter of Example 1, wherein the identification engine is to determine whether the gas is present in a first predefined concentration range based at least in part on a plurality of resistance measurements using a multiple linear regression model and the identification engine is to determine whether the gas is present in a second predefined concentration range based at least in part on the plurality of resistance measurements using the one or more artificial neural networks.

Example 4 may include the subject matter of any one of Examples 1-3, wherein the set of heterogenous MOS sensors includes a first MOS sensor element made of a first metal-oxide material and a second MOS sensor element made of a second metal-oxide material different than the first metal-oxide material, and wherein the identification engine is to determine whether the gas is present in the first predefined concentration range based at least in part on a first resistance measurement from the first MOS sensor element and a second resistance measurement from the second MOS sensor element.

Example 5 may include the subject matter of Example 4, wherein the first resistance measurement corresponds to operation of the first MOS sensor element at a first temperature and the second resistance measurement corresponds to operation of the second MOS sensor element at a second temperature different than the first temperature.

Example 6 may include the subject matter of any one of Examples 4-5, wherein the first MOS sensor element has a first MOS active material that includes indium oxide ($In_2O_3$), Tin Oxide ($SnO_2$), Tungsten Oxide ($WO_3$), or Zinc Oxide (ZnO) and the second MOS sensor element has a second MOS active material that includes $In_2O_3$, $SnO_2$, $WO_3$, or ZnO.

Example 7 may include the subject matter of any one of Examples 1-6, further comprising a wireless communication module coupled with the identification engine, wherein the identification engine is to determine an estimated concentration of the gas using one or more of a multiple linear regression model and the one or more artificial neural networks and send an indication corresponding to the estimated concentration to a sensor monitoring system using the wireless communication module.

Example 8 may include a method of identifying a gas comprising: measuring resistance, during exposure to a gas mixture, of a first metal oxide semiconductor (MOS) sensor element having a first MOS active material at a first temperature to produce a first resistance measurement; measuring resistance, during exposure to the gas mixture, of a second MOS sensor element having a second MOS active material at a second temperature different than the first temperature to produce a second resistance measurement; determining whether the gas mixture includes a gas in a first predefined concentration range based at least in part on the first resistance measurement; and determining whether the gas mixture includes the gas in a second predefined concentration range based at least in part on the second resistance measurement.

Example 9 may include the subject matter of Example 8, wherein the first MOS sensor element and the second MOS sensor element are the same sensor element.

Example 10 may include the subject matter of Example 8, wherein the first MOS sensor element and the second MOS sensor element are different sensor elements.

Example 11 may include the subject matter of any one of Examples 8-10, wherein determining whether the gas mixture includes the gas in the first predefined concentration range includes generating a determination based at least in part on a multiple linear regression model.

Example 12 may include the subject matter of any one of Examples 8-11, wherein determining whether the gas mixture includes the gas in the second predefined concentration range includes generating a determination with an artificial neural network.

Example 13 may include the subject matter of any one of Examples 8-12, further comprising: measuring resistance, during exposure to the gas mixture, of one or more additional MOS sensor elements in a first set of MOS sensor elements; and measuring resistance, during exposure to the gas mixture, of one or more additional MOS sensor elements in a second set of MOS sensor elements, wherein determining whether the gas mixture includes the gas in the first predefined concentration range is also based at least in part on the one or more additional resistance measurements from the first set of MOS sensor elements, wherein determining whether the gas mixture includes the gas in the second predefined concentration range is also based at least in part on the one or more additional resistance measurements from the second set of MOS sensor elements, wherein the first set of MOS sensor elements does not include the first MOS sensor element, and wherein the second set of MOS sensor elements does not include the second MOS sensor element.

Example 14 may include the subject matter of any one of Examples 8-13, wherein the gas is a first gas and the method further comprises: measuring resistance, during exposure to the gas mixture, of a third MOS sensor element operating at a third temperature to produce a third resistance measurement; measuring resistance, during exposure to the gas mixture, of a fourth MOS sensor element operating at a fourth temperature different than the third temperature to produce a fourth resistance measurement; determining whether the gas mixture includes a second gas in a third predefined concentration range based at least in part on the third resistance measurement, wherein the second gas is different than the first gas; and determining whether the gas mixture includes the second gas in a fourth predefined concentration range based at least in part on the fourth resistance measurement.

Example 15 may include a method of training a hybrid multi-staged machine learning system for gas identification comprising: sensing, with a first set of metal oxide semiconductor (MOS) sensor elements operating at a first temperature, a first set of gas mixtures having a first gas at a first set of known concentrations; receiving a first set of resistance measurements from the first set of MOS sensor elements, wherein the first set of resistance measurements corresponds to the sensed first set of known concentrations; sensing, with a second set of MOS sensor elements operating at a second temperature different than the first temperature, a second set of gas mixtures having the first gas at a second set of known concentrations; receiving a second set of resistance measurements from the second set of MOS sensor elements, wherein the second set of resistance measurements corresponds to the sensed second set of known concentrations; generating a first data model and a second data model based at least in part on the first set of resistance measurements, the first set of known concentrations, the second set of resistance measurements, and the second set of known concentrations, wherein the first data model fits a first concentration range of the first gas better than the second data model with respect to a first predefined fit metric, and the second data model fits a second concentration range of the first gas better than the first model with respect to a second predefined fit metric.

Example 16 may include the subject matter of Example 15, wherein the first data model is a multiple linear regression data model and the first predefined fit metric is a coefficient of multiple determination.

Example 17 may include the subject matter of any one of Examples 15-16, wherein the second data model is an artificial neural network.

Example 18 may include the subject matter of any one of Examples 15-17, wherein the first set of MOS sensor elements includes two or more MOS sensor elements made of different MOS materials and the second set of MOS sensor elements includes two or more MOS sensor elements made of different MOS materials.

Example 19 may include the subject matter of any one of Examples 15-18, wherein the first set of MOS sensor elements includes the second set of MOS sensor elements.

Example 20 may include the subject matter of any one of Examples 15-19, wherein generating the first data model is based at least in part on a set of normalized resistances, wherein each normalized resistance in the set of normalized resistances is a ratio of a MOS resistance measurement from a MOS sensor in the presence of the gas mixture over a baseline resistance measurement of the same MOS sensor in the presence of air.

Example 21 may include one or more non-transitory computer-readable media comprising instructions that cause an apparatus, in response to execution of the instructions by the apparatus, to: determine, with a linear regression model, whether a gas mixture includes a gas in a first predefined concentration range based at least in part on a first resistance measurement received from a first metal oxide semiconductor (MOS) sensor element exposed to the gas mixture to produce a first concentration indicator; and determine, with one or more artificial neural networks, whether the gas mixture includes the gas in a second predefined concentration range based at least in part on a second resistance measurement received from a second MOS sensor element exposed to the gas mixture to produce a second concentration indicator in response to the first concentration indicator indicates the gas is included in the gas mixture in the first predefined concentration range.

Example 22 may include the subject matter of Example 21, wherein the apparatus includes a gas identification device that includes the first MOS sensor element and the second MOS sensor element.

Example 23 may include the subject matter of any one of Examples 21-22, wherein the first MOS sensor element and the second MOS sensor element are different sensor elements.

Example 24 may include the subject matter of any one of Examples 21-23, wherein the instructions are also to cause the apparatus to: determine whether the gas mixture includes the gas in the first predefined concentration range based at least in part on one or more additional resistance measurements received from a first set of MOS sensor elements; and determine whether the gas mixture includes the gas in the second predefined concentration range based at least in part on one or more additional resistance measurements received from a second set of MOS sensor elements, wherein the first set of MOS sensor elements does not include the first MOS sensor element, and wherein the second set of MOS sensor elements does not include the second MOS sensor element.

Example 25 may include the subject matter of any one of Examples 21-24, wherein the linear regression model is a first linear regression model and the instructions are further to cause the apparatus to determine, with a second linear regression model, whether the gas mixture includes a second gas in a third predefined concentration range based at least in part on a resistance measurement received from a MOS sensor element operating at a temperature different than an operating temperature of the first MOS sensor element.

Example 26 may include the subject matter of Example 21, wherein one or more of the determine, with a linear regression model, whether the gas mixture includes the gas in the first predefined concentration range and the determine, with one or more artificial neural networks, whether the gas mixture includes the gas in the second predefined concentration range, is performed on a cloud server remote from the first MOS sensor element and the second MOS sensor element.

Example 27 may include a gas identification apparatus comprising: means for measuring resistance, during exposure to a gas mixture, of a first metal oxide semiconductor (MOS) sensor element operating at a first temperature to produce a first resistance measurement; means for measuring resistance, during exposure to the gas mixture, of a second MOS sensor element operating at a second temperature different than the first temperature to produce a second resistance measurement; means for determining whether the gas mixture includes a gas in a first predefined concentration range based at least in part on the first resistance measurement; and means for determining whether the gas mixture includes the gas in a second predefined concentration range based at least in part on the second resistance measurement.

Example 28 may include the subject matter of Example 27, wherein the first MOS sensor element and the second MOS sensor element are the same sensor element.

Example 29 may include the subject matter of Example 27, wherein the first MOS sensor element and the second MOS sensor element are different sensor elements.

Example 30 may include the subject matter of any one of Examples 27-29, wherein the means for determining whether the gas mixture includes the gas in the first predefined concentration range includes means for generating a determination based at least in part on a multiple linear regression model.

Example 31 may include the subject matter of any one of Examples 27-30, wherein the means for determining whether the gas mixture includes the gas in the second predefined concentration range includes means for generating a determination with an artificial neural network.

Example 32 may include the subject matter of any one of Examples 27-31, further comprising: means for measuring resistance, during exposure to the gas mixture, of one or more additional MOS sensor elements in a first set of MOS sensor elements; means for measuring resistance, during exposure to the gas mixture, of one or more additional MOS sensor elements in a second set of MOS sensor elements, wherein determining whether the gas mixture includes the gas in the first predefined concentration range is also based at least in part on the one or more additional resistance measurements from the first set of MOS sensor elements, wherein determining whether the gas mixture includes the gas in the second predefined concentration range is also based at least in part on the one or more additional resistance measurements from the second set of MOS sensor elements, wherein the first set of MOS sensor elements does not include the first MOS sensor element, and wherein the second set of MOS sensor elements does not include the second MOS sensor element.

Example 33 may include the subject matter of any one of Examples 27-32, wherein the gas is a first gas and the apparatus further comprises: means for measuring resistance, during exposure to the gas mixture, of a third MOS sensor element operating at a third temperature to produce a third resistance measurement; means for measuring resistance, during exposure to the gas mixture, of a fourth MOS sensor element operating at a fourth temperature different than the third temperature to produce a fourth resistance measurement; means for determining whether the gas mixture includes a second gas in a third predefined concentration range based at least in part on the third resistance, wherein the second gas is different than the first gas; and means for determining whether the gas mixture includes the second gas in a fourth predefined concentration range based at least in part on the fourth resistance measurement.

Various embodiments may include any suitable combination of the above-described embodiments including alternative (or) embodiments of embodiments that are described in conjunctive form (and) above (e.g., the "and" may be "and/or"). Furthermore, so me embodiments may include one or more articles of manufacture (e.g., non-transitory computer-readable media) having instructions, stored thereon, that when executed result in actions of any of the above-described embodiments. Moreover, some embodiments may include apparatuses or systems having any suitable means for carrying out the various operations of the above-described embodiments.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:

1. A gas identification apparatus, comprising:
    a set of heterogeneous metal oxide semiconductor (MOS) sensors to provide different response patterns for the presence of different gases; and
    an identification engine coupled with the sensors, and having a plurality of regression models and one or more artificial neural networks, to analyze a response pattern to identify presence of a gas, based at least in part on a plurality of property measurements of the MOS sensors when exhibiting the response pattern, and using one or more of the plurality of regression models and the one or more artificial neural networks;
    wherein the identification engine is to determine whether the gas is present in a first predefined concentration range based at least in part on a plurality of resistance measurements using a multiple linear regression model, and the identification engine is to determine whether the gas is present in a second predefined concentration range based at least in part on the plurality of resistance measurements using the one or more artificial neural networks.

2. The gas identification apparatus of claim 1, wherein the set of heterogeneous MOS sensors includes a first MOS sensor element made of a first metal-oxide material and a second MOS sensor element made of a second metal-oxide material different than the first metal-oxide material, and wherein the identification engine is to determine whether the gas is present in the first predefined concentration range based at least in part on a first resistance measurement from the first MOS sensor element and a second resistance measurement from the second MOS sensor element.

3. The gas identification apparatus of claim 2, wherein the first resistance measurement corresponds to operation of the first MOS sensor element at a first temperature and the second resistance measurement corresponds to operation of the second MOS sensor element at a second temperature different than the first temperature.

4. The gas identification apparatus of claim 2, wherein the first MOS sensor element has a first MOS active material that includes indium oxide (In2O3), Tin Oxide (SnO2), Tungsten Oxide (WO3), or Zinc Oxide (ZnO) and the second MOS sensor element has a second MOS active material that includes In2O3, SnO2, WO3, or ZnO.

5. The gas identification apparatus of claim 1, further comprising a wireless communication module coupled with the identification engine, wherein the identification engine is to send results of the determinations to a sensor monitoring system using the wireless communication module.

6. A method of identifying a gas comprising:
    measuring resistance, during exposure to a gas mixture, of a first metal oxide semiconductor (MOS) sensor element having a first MOS active material at a first temperature to produce a first resistance measurement;
    measuring resistance, during exposure to the gas mixture, of a second MOS sensor element having a second MOS active material at a second temperature different than the first temperature to produce a second resistance measurement;
    determining whether the gas mixture includes a gas in a first predefined concentration range based at least in part on the first resistance measurement; and
    determining whether the gas mixture includes the gas in a second predefined concentration range based at least in part on the second resistance measurement;
    wherein determining whether the gas mixture includes the gas in the first predefined concentration range includes generating a determination based at least in part on a multiple linear regression model; and
    wherein determining whether the gas mixture includes the gas in the second predefined concentration range includes generating a determination with an artificial neural network.

7. The method of claim 6, wherein the first MOS sensor element and the second MOS sensor element are the same sensor element.

8. The method of claim 6, wherein the first MOS sensor element and the second MOS sensor element are different sensor elements.

9. The method of claim 6, further comprising:
measuring resistance, during exposure to the gas mixture, of one or more additional MOS sensor elements in a first set of MOS sensor elements; and
measuring resistance, during exposure to the gas mixture, of one or more additional MOS sensor elements in a second set of MOS sensor elements,
wherein determining whether the gas mixture includes the gas in the first predefined concentration range is also based at least in part on one or more additional resistance measurements from the first set of MOS sensor elements, wherein determining whether the gas mixture includes the gas in the second predefined concentration range is also based at least in part on the one or more additional resistance measurements from the second set of MOS sensor elements, wherein the first set of MOS sensor elements does not include the first MOS sensor element, and wherein the second set of MOS sensor elements does not include the second MOS sensor element.

10. The method of claim 6, wherein the gas is a first gas and the method further comprises:
measuring resistance, during exposure to the gas mixture, of a third MOS sensor element operating at a third temperature to produce a third resistance measurement;
measuring resistance, during exposure to the gas mixture, of a fourth MOS sensor element operating at a fourth temperature different than the third temperature to produce a fourth resistance measurement;
determining whether the gas mixture includes a second gas in a third predefined concentration range based at least in part on the third resistance measurement, wherein the second gas is different than the first gas; and
determining whether the gas mixture includes the second gas in a fourth predefined concentration range based at least in part on the fourth resistance measurement.

11. One or more non-transitory computer-readable media comprising instructions that cause an apparatus, in response to execution of the instructions by the apparatus, to:
determine, with a linear regression model, whether a gas mixture includes a gas in a first predefined concentration range based at least in part on a first resistance measurement received from a first metal oxide semiconductor (MOS) sensor element exposed to the gas mixture to produce a first concentration indicator; and
determine, with one or more artificial neural networks, whether the gas mixture includes the gas in a second predefined concentration range based at least in part on a second resistance measurement received from a second MOS sensor element exposed to the gas mixture to produce a second concentration indicator in response to the first concentration indicator indicating the gas is included in the gas mixture in the first predefined concentration range.

12. The one or more non-transitory computer-readable media of claim 11, wherein the apparatus includes a gas identification device that includes the first MOS sensor element and the second MOS sensor element.

13. The one or more non-transitory computer-readable media of claim 11, wherein the first MOS sensor element and the second MOS sensor element are different sensor elements.

14. The one or more non-transitory computer-readable media of claim 11, wherein the instructions are also to cause the apparatus to:
determine whether the gas mixture includes the gas in the first predefined concentration range based at least in part on one or more additional resistance measurements received from a first set of MOS sensor elements; and
determine whether the gas mixture includes the gas in the second predefined concentration range based at least in part on one or more additional resistance measurements received from a second set of MOS sensor elements, wherein the first set of MOS sensor elements does not include the first MOS sensor element, and wherein the second set of MOS sensor elements does not include the second MOS sensor element.

15. The one or more non-transitory computer-readable media of claim 14, wherein the linear regression model is a first linear regression model and the instructions are further to cause the apparatus to determine, with a second linear regression model, whether the gas mixture includes a second gas in a third predefined concentration range based at least in part on a resistance measurement received from a MOS sensor element operating at a temperature different than an operating temperature of the first MOS sensor element.

16. The one or more non-transitory computer-readable media of claim 11, wherein one or more of the determine, with a linear regression model, whether the gas mixture includes the gas in the first predefined concentration range and the determine, with one or more artificial neural networks, whether the gas mixture includes the gas in the second predefined concentration range, is performed on a cloud server remote from the first MOS sensor element and the second MOS sensor element.

* * * * *